United States Patent [19]

Feldman et al.

[11] Patent Number: 5,019,583
[45] Date of Patent: May 28, 1991

[54] N-PHENYL-N-(4-PIPERIDINYL)AMIDES USEFUL AS ANALGESICS

[75] Inventors: Paul L. Feldman, Durham; Michael K. James, Raleigh; Marcus F. Brackeen, Durham; Michael R. Johnson; Harry J. Leighton, both of Chapel Hill, all of N.C.

[73] Assignee: Glaxo Inc., Research Triangle Park, N.C.

[21] Appl. No.: 448,497

[22] Filed: Dec. 11, 1989

Related U.S. Application Data

[63] Continuation-in-part of Ser. No. 311,311, Feb. 15, 1989, abandoned.

[51] Int. Cl.$^5$ .................. A61K 31/445; C07D 211/58
[52] U.S. Cl. .................. 514/327; 514/329; 544/244
[58] Field of Search ............... 546/224; 514/329, 327

[56] References Cited

U.S. PATENT DOCUMENTS

| | | | |
|---|---|---|---|
| 3,164,600 | 10/1961 | Janssen | 546/224 |
| 3,998,834 | 1/1976 | Janssen et al. | 546/224 |
| 4,167,574 | 10/1978 | Janssens | 546/194 |
| 4,179,569 | 12/1977 | Janssen et al. | 546/223 |
| 4,584,303 | 4/1985 | Huang et al. | 546/326 |
| 4,801,721 | 12/1986 | Ryan et al. | 548/411 |

FOREIGN PATENT DOCUMENTS 309043 9/1987 European Pat. Off. .

OTHER PUBLICATIONS

Srulevitch et al, Design, Synthesis and Sar of Analgesics, OSAR 1989, pp. 377-381.

Primary Examiner—Richard L. Raymond
Assistant Examiner—Mark W. Russell
Attorney, Agent, or Firm—Salvatore R. Conte

[57] ABSTRACT

N-Phenyl-N-(4-piperdinyl)amide derivatives are disclosed having the general formula (I):

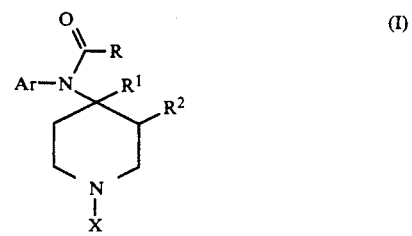

wherein X is a member selected from the group consisting of alkoxy-carbonyl-lower alkyl, lower alkyl-carbonyloxy-lower alkyl, alkenyloxy-carbonyl-lower alkyl, and $(C_{1-2})$alkoxy-$(C_{1-2})$-alkoxy-carbonyl-lower alkyl, and Ar, R, $R^1$ and $R^2$ are defined hereinafter, including isomeric forms thereof and acid addition salts thereof. The compounds exhibit analgesic activity having relatively short durations of analgesic action. The invention embraces the compounds (I), pharmaceutical compositions of (I) and methods of providing analgesia with (I). Also included are certain novel intermediates for making (I).

47 Claims, No Drawings

N-PHENYL-N-(4-PIPERIDINYL)AMIDES USEFUL AS ANALGESICS

This application is a continuation-in-part of co-pending U.S. Ser. No. 07/311,311 filed Feb. 15, 1989 now abandoned.

BACKGROUND OF THE INVENTION

The invention pertains to the field of N-phenyl-N-(4-piperidinyl)amides having potent analgesic activity. A number of patents disclose certain N-phenyl-N-(4-piperidinyl)amides having analgesic activity such as, for example, U.S. Pat. Nos. 3,164,600; 3,998,834; 4,179,569; 4,584,303; and 4,167,574. The analgesic compounds of this invention differ structurally from the prior art compounds by the particular N-substituent on the piperidine ring, i.e., the "X" function indicated in the hereafter formula (I) compounds. In general, they also differ by their relatively short durations of analgesic action, ranging from the ultra short to medium range, and their non-hepatic means of inactivation. The invention also provides certain novel synthetic intermediates for making formula (I) compounds.

DETAILED DESCRIPTION OF THE INVENTION

The invention relates to novel chemical compounds and pharmaceutical compositions thereof. More particularly, the subject chemical compounds are N-phenyl-N-(4-piperidinyl)amides represented by the formula:

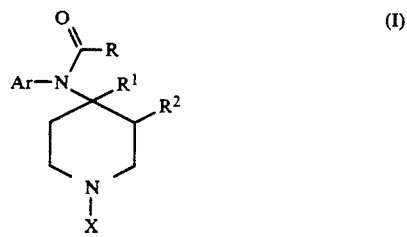

(I)

wherein:
X is a member selected from the group consisting of: alkoxy-carbonyl-lower alkyl (preferred), lower alkyl-carbonyloxy-lower alkyl, alkenyloxy-carbonyl-lower alkyl, and ($C_{1-2}$)alkoxy-($C_{1-2}$)alkoxy-carbonyl-lower alkyl.
Ar is a member selected from the group consisting of phenyl (preferred) and mono-, di- and tri-substituted phenyl, preferably mono-substituted in the 2-position, wherein each substituent is independently selected from the group consisting of halo, lower alkyl, lower alkoxy and trifluoromethyl;
R is a member selected from the group consisting of lower alkyl, preferably ethyl, and lower alkoxy-lower alkyl, preferably methoxymethyl;
$R^1$ is a member selected from the group consisting of hydrogen, lower alkoxy-carbonyl, preferably methoxycarbonyl, and methoxymethyl; and
$R^2$ is a member selected from the group consisting of hydrogen and methyl;
and the optically active and cis-trans isomers thereof, and the acid addition salts, preferably the pharmaceutically acceptable acid addition salts, of said compounds and isomers.

An additional aspect of the subject invention relates to certain novel acidic intermediates which are useful in the synthesis of certain formula (I) compounds. Said intermediates are represented by formula (A) wherein $X_a$ is a carboxy-lower alkyl substituent on the ring nitrogen, replacing the aforementioned X-substituent in formula (I):

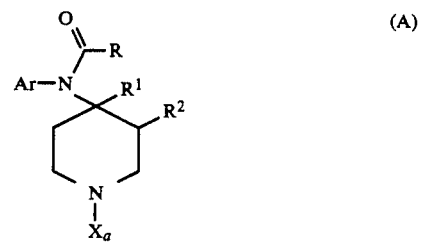

(A)

As used in the foregoing definitions the term "lower" is meant to modify the so-indicated group by indicating from 1 to 4 carbon atoms; the terms "alkyl", "alkoxy" and "alkenyl" are each meant to respectively include straight and branch chained hydrocarbons, e.g. of about 1 to 10 carbons and include the group of hydrocarbons of 1 to 4 carbons; and the term "halo" is generic to halogens of atomic weight less than 127, i.e., fluoro (preferred), chloro, bromo and iodo.

The formula (I) compounds of the invention provide potent analgesia with a duration of action ranging from ultra-short to medium. Such activity is characterized by rapid onset and a half-life generally ranging from about 5 to about 40 minutes in experimental rats. In contrast, the well-known narcotic analgesic, N-(1-phenethyl-4-piperidyl) propionanilide, generically known as fentanyl, and its congeners, sufentanil and alfentanil, have durations of action of 60, 80 and 55 minutes in rats, respectively, and terminal half-lives in humans of about 1.5 to 7 (16 for geriatric patients), 2.5 and 1.2 to 3 hours, respectively (Mather, L. E., Clinical Pharmacokinetics, 1983, 8:422-446). The marked potency and very short duration of analgesia provided by the ultra-short acting compounds of this invention are highly desirable in circumstances where severe pain has to be eliminated over a short period of time, e.g., anesthesiology. With the current preponderance of short surgical procedures and the growing trend towards outpatient surgery, there exists an urgent need for a powerful but short acting analgesic as stated by Dr. Paul A. J. Janssen in Janssen: Opioids in Anesthesia. (Estafanous, F. G., ed.) Butterworth, Boston. (1984). The compounds of the invention can be used together with a pharmaceutically acceptable carrier to provide pharmaceutical compositions and can be administered to mammals such as man in amounts sufficient to provide analgesic effects.

When X is alkoxy-carbonyl-lower alkyl, e.g. lower alkoxy-carbonyl-lower alkyl, compounds wherein the carbon of the alkoxy directly attached to the oxygen of the alkoxy is a methylene or methyl group, i.e. wherein it is substituted by no more than 1 alkyl group, are generally shorter acting. Further, the lower alkyl of the alkoxy-carbonyl-lower alkyl is, in particular, ethyl of the formula $-CH_2CH_2-$.

The formula (I) compounds may be converted to the therapeutically active acid addition salt form by treatment with an appropriate acid, such as, for example, an inorganic acid, such as hydrohalic acid, e.g., hydrochloric, hydrobromic, and the like, and sulfuric acid, nitric acid, phosphoric acid and the like; or an organic acid, such as, for example, acetic, propanoic, hydroxyacetic, α-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxy-benzeneacetic, methanesulfonic, ethanesulfonic, benzenesulfonic, 4-methylbenzenesulfonic, cyclohexanesulfamic, α-hydroxybenzoic, 4-amino-2-hydroxybenzoic and the like acids. Conversely, the salt form can be converted by treatment with alkali into the free base form. In addition, the salt forms may be useful in the preparation of other salt forms, for example, as intermediates for conversion into the preferred pharmaceutically acceptable salt derivatives. Furthermore, the particular salt may exist as a solvate, e.g., a hydrate or a hemihydrate.

Several of the compounds of formula (I) have one or more asymmetric carbon atoms in their structure and consequently they may exist in the form of different optical isomeric forms or mixtures e.g., racemates, of such forms. When R² in formula (I) represents a methyl group there are two asymmetric carbon atoms in the piperidine ring. Additional asymmetric carbon atoms may also be present in the X-substituent, for example, when X is —CH(CH₃)CH₂COOCH₃, —CH₂CH(CH₃)COOCH₃ and —CH₂COOCH₂CH(CH₃)CH₂CH₃. Enantiomeric forms and mixtures of such forms may be obtained separately by the application of methods of resolution known to those skilled in the art such as, for example, salt formation with an optically active acid followed by selective crystallization or chiral derivatization and in turn followed by selective crystallization or silica gel chromatography.

When R² is a methyl group, the relative position of said methyl group and of the substituents in the 4-position of the piperidine ring with respect to the plane of the piperidine ring may be cis or trans, according to the rules of nomenclature described in "Naming and Indexing of Chemical Substances for C.A. during the Ninth Collective Period (1972-1976) p. 861." Compounds of formula (I) having the cis- or trans-configuration, essentially free of the other, may be obtained, for example, by starting their preparation from pure cis- or trans-isomers of the appropriate precursors. When, for example, an intermediate of formula (XI) in which R² stands for methyl is subjected to a selective crystallization, cis- and trans-isomers are obtained separately and the thus-obtained forms are conveniently used in the further synthesis of compounds of formula (I) having the corresponding configuration. Alternatively, substantially pure forms of the cis- and trans-isomer of compounds of formula (I) may be obtained, substantially free of the other isomer, by separating a mixture of such appropriate precursor forms (e.g., see Formula XXI hereinafter) by silica gel chromatography.

Cis- and trans-forms may in turn be further resolved into their optical enantiomers, each essentially free of its optical counterpart, by the application of art-known methodologies such as noted previously.

All racemic and isomeric forms of the compounds of formula (I), including diastereomeric mixtures, pure diastereomers and enantiomers, and mixtures thereof, are intended to be within the scope of this invention.

The compounds of formula (I) may generally be prepared by introducing the X substituent on to the piperidine ring nitrogen of an intermediate of the formula (11):

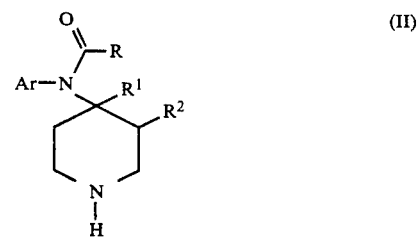

wherein Ar, R, R¹ and R² are as previously defined, by the application of conventional methodologies known in the art. Depending on the nature of the X substituent, the following methods may be utilized therefor.

The compounds of formula (II) are known compounds which are obtainable by art recognized procedures. In addition, the compounds of formula (II) in which R² is methyl and R¹ is hydrogen have been prepared (see examples hereinafter) from 1-methoxy-carbonyl-3-methyl-4-[1-oxopropylaryl-amino]piperidines, which are in turn prepared from 3-methoxycarbonyl 4-piperidinone hydrochloride using the procedure described by W. F. M. VanBerer et al., J. Med. Chem. 1974, 17, 1047 and T. R. Burke, Jr., et al., J. Med. Chem. 1986, 29, 1087.

The introduction of the aforementioned X groups on to the ring nitrogen of (II) may conveniently be carried out by the alkylation reaction of (II) with an appropriate halide of formula (III) wherein "Hal" is bromo (preferred), chloro or iodo and X represents the aforementioned groups as shown in Scheme I:

Scheme I

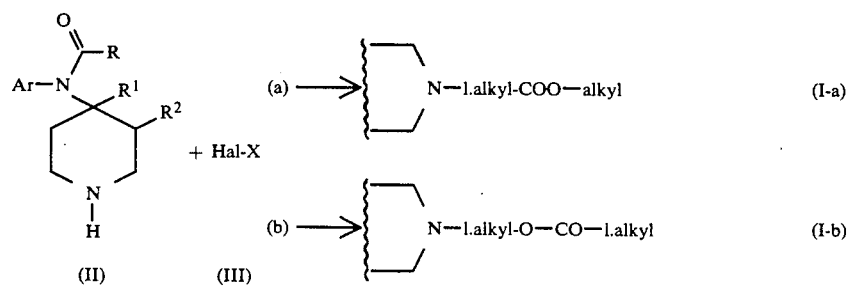

-continued
Scheme I

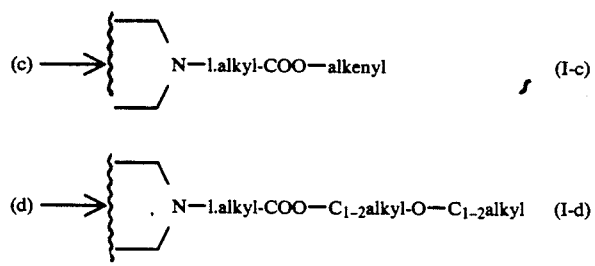

Formulae (Ia)-(Id) and other formuale utilize the convention of partial structures to denote the remainder of the formula as in formula (I) hereinabove.

The alkylation reaction of (II) with (III) is conveniently conducted in an inert organic solvent such as, for example, acetonitrile (preferred), an aromatic hydrocarbon, e.g., benzene, methylbenzene, dimethylbenzene and the like; a lower alkanol, e.g., methanol, ethanol, 1-butanol and the like; a ketone, e.g , 4-methyl-2-pentanone and the like; an ether, e.g., 1,4-dioxane, tetrahydrofuran (THF), 1,1-oxybisethane and the like; N,N-dimethylformamide (DMF); nitrobenzene; and the like. The addition of an appropriate base such as, for example, an alkali metal carbonate or bicarbonate, preferably potassium carbonate, may be utilized to neutralize the acid that is liberated during the course of the reaction. In some circumstances, the addition of an iodide salt, preferably an alkali metal iodide such as sodium iodide, is appropriate. Ambient temperatures (22°-25° C.) are generally sufficient, although somewhat higher temperatures may be employed to enhance the rate of the reaction.

When X is alkoxy-carbonyl-ethyl, wherein the ethyl may be substituted with 1 or 2 $C_{1-2}$ alkyl groups for a total of 2-4 carbons, an alternative method of introducing this group on to the ring nitrogen of (II) to yield (V) is by way of a conjugate addition reaction between (II) and an α,β-unsaturated carbonyl reactant of formula (IV) in an inert organic solvent such as, for example, acetonitrile, a lower alkanol, e.g., methanol, ethanol and the like, an ether, e.g., diethyl ether, dioxane and the like; and an aromatic hydrocarbon, e.g., benzene, toluene and the like as shown, for example, in Scheme II.

Scheme II

-continued
Scheme II

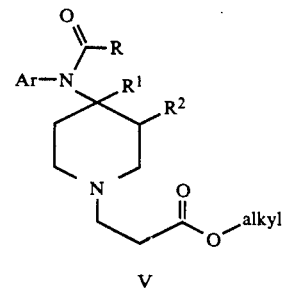

V

When X is alkoxy-carbonyl-loweralkyl in (I-a) or alkenyloxy-carbonyl-loweralkyl in (I-c), an alternative method of introducing said X-substituent onto the piperidine nitrogen is by esterification of the corresponding acidic formula (A) compounds, i.e., formula (I) wherein X is carboxy-loweralkyl such as (VI), using the appropriate alkyl or alkenyl N,N-diisopropyl-pseudourea in an organic solvent, for example, chloroform, at ambient to reflux temperatures. The acids of formula (A), e.g. where $X_a$ is a carboxyethyl thus defining (VI), are believed to be novel intermediates, may be obtained by reacting (II) with an appropriate t-butyl ester of formula (III) or tertiary butyl acrylate (Michael Reaction) followed by reacting the thus-obtained product, e.g. (VII), with excess trifluoroacetic acid at 0° C. to ambient temperatures according to the following Scheme III:

Scheme III

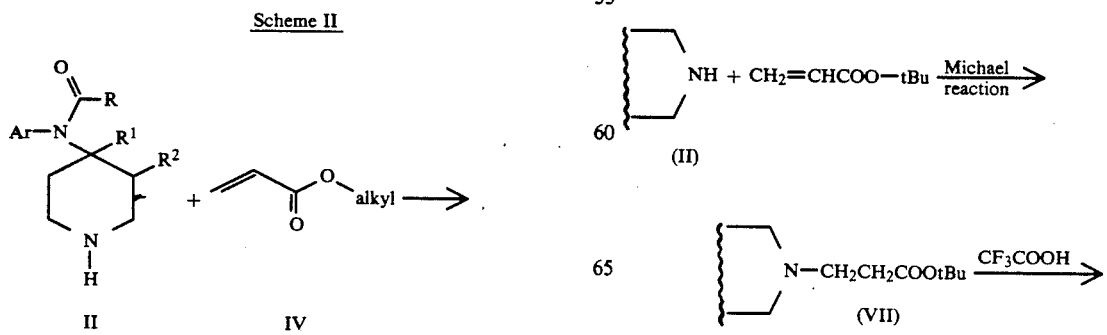

-continued
Scheme III

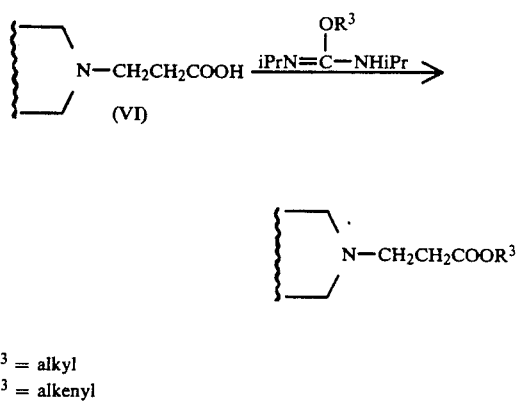

(I-a) R³ = alkyl
(I-c) R³ = alkenyl

The ester CH₂=CHCOO—tBu in Scheme III may be substituted by other esters e.g. of the formula $R^4R^5C=CR^6COO-tBu$ wherein $R^4$, $R^5$ and $R^6$ are hydrogen methyl or ethyl provided that the total carbons in $R^4$, $R^5$ and $R^6$ is 0–2, to yield other acids of Formula (A).

Alternatively, the appropriate carboxy loweralkyl halide or acrylic acid, the acrylic acid embodiment being shown below, can be esterified with the appropriate alkyl or alkenyl-N,N-diisopropyl-pseudourea, for example, in chloroform at ambient to reflux temperatures, to yield the corresponding formula (III) halide ester or acrylic ester which is then introduced onto the ring nitrogen of a formula (II) compound by means of the previously mentioned alkylation reaction or conjugate addition Michael reaction, as shown in Scheme IV:

Scheme IV

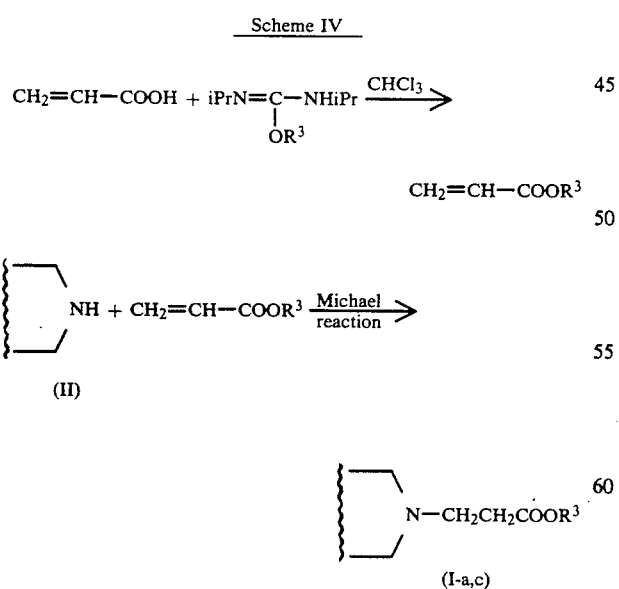

In both Scheme III and IV, when R³ is alkenyl, the double bond is not directly attached to the oxygen of the OR³. In addition, the CH2=CH-COOH starting material may be substituted by $R^4R^5C=CR^6COOH$ wherein $R^4$, $R^5$ and $R^6$ are as defined above. An alternative method of preparing the formula (I) compounds wherein X is loweralkyl-carbonyloxy-loweralkyl and $R^1$ is hydrogen or methoxymethyl is by reduction of the corresponding ester (I-a) to the corresponding alcohol (VIII), for example, by conventional lithium aluminum hydride reduction in ether solution, preferably THF, at ambient temperatures. The thus-obtained alcohol (VIII) is then transformed into the reverse ester (IX) by reaction with an appropriate loweralkyl anhydride, for example, acetic acid anhydride, propionic acid anhydride, and the like, in an organic solvent such as pyridine. This is shown in the following Scheme V wherein X is in formula (I-a) is loweralkyl-CO₂-loweralkyl:

Scheme V

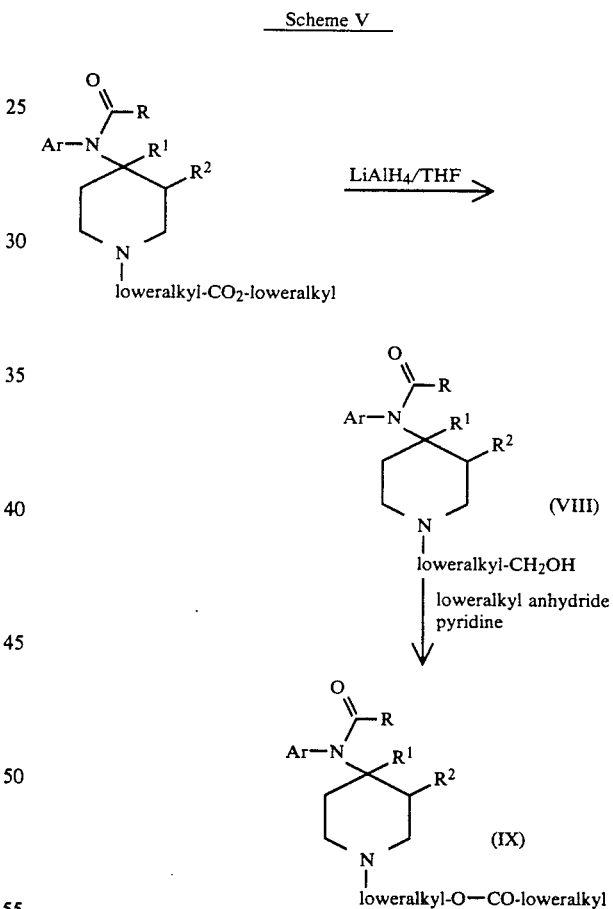

When X is $C_{1-2}$alkoxy-$C_{1-2}$alkoxy-carbonyl-ethyl, wherein the ethyl may be substituted with 1 or 2 $C_{1-2}$ alkyl groups for a total of 2–4 carbons, the introduction of this group on to the ring nitrogen of (II) may conveniently be carried out by the reaction of (II) with an α,β-unsaturated carbonyl reactant of formula (X) according to standard Michael Reaction conditions and solvents, acetonitrile being preferred, to yield the corresponding N-substituted product (V-a) as shown in Scheme VI:

Scheme VI

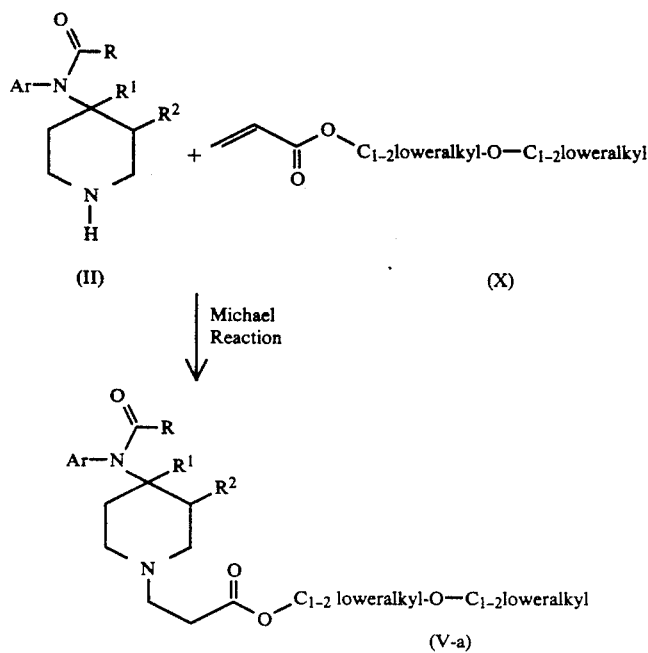

The compounds of formula (X) having a $C_{1-2}$alkoxy-methoxy-carbonyl-ethyl function are obtained by the reaction of acrylic acid with an appropriate dialkoxyalkane such as dimethoxymethane and diethoxymethane in the presence of phosphorous pentoxide. The acrylic acid may be substituted by other acids of the formula $R^4R^5C=CR^6COOH$ to yield other products within the invention. The compounds of formula (X) having a $C_{1-2}$alkoxy-ethoxy-carbonyl-loweralkyl function are available from commercial suppliers.

As noted previously, the formula (I) compounds are capable of existence in diastereomeric and enantiomeric forms. The following schematic descriptions exemplify particular synthetic paths for preparing such diastereomers and enantiomers as pure materials starting with appropriate precursors.

Scheme VII

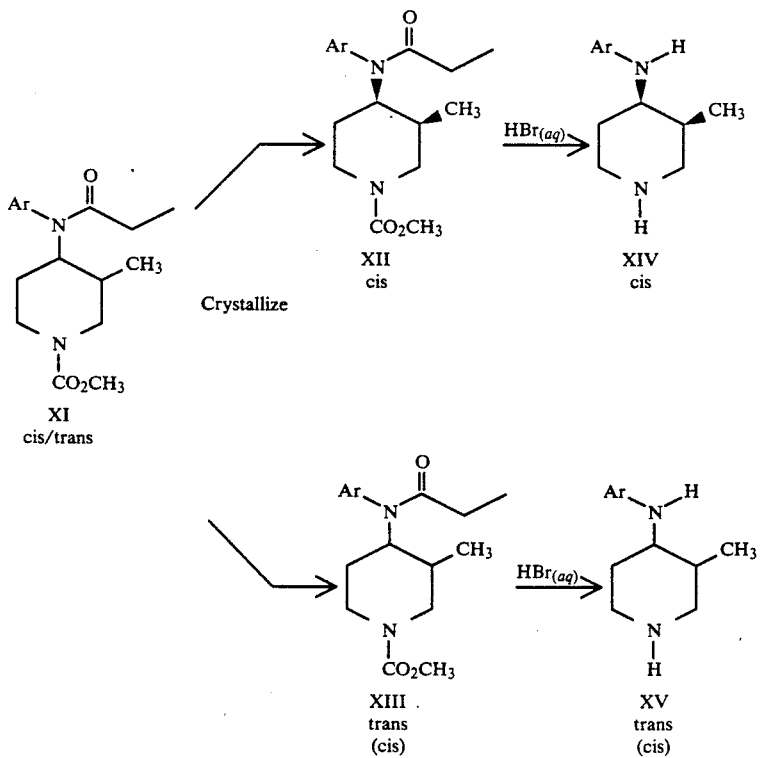

As depicted in Scheme VII, the cis/trans mixture (XI) is conveniently used as the starting material. Standard crystallization procedures using organic solvents such as ethyl actate, ether/hexane and the like, affords separation of the corresponding pure cis isomer (XII) in crystalline form and the corresponding trans isomer (XIII) in the mother liquor with some residual cis isomer. The pure cis isomer (XII), essentially free of the corresponding trans isomer, and the predominantly trans isomer (XIII) are each converted to the corresponding 3-methyl-4-arylaminopiperidines of respective formulas (XIV) and (XV) by treatment with a concentrated hydrohalic acid (hydrobromic acid preferred) at reflux temperature. Subsequently, the resultant pure crystalline cis isomer (XIV) may then be recovered and utilized in the further synthetic pathways depicted in Scheme VIII to obtain the formula (1) final products in the corresponding cis form.

As shown in pathway 1 of Scheme VIII, the cis precursor (XIV) is subjected to the previously described alkylation reaction with a formula (III) halide to yield the corresponding N-substituted compounds of formula (XVI). Acylation of the arylamino group in (XVI) with an appropriate acid chloride (RCOCl in which R is as previously defined) provides the respective formula (I) compounds in cis form. The acylation reaction is conveniently carried out utilizing an appropriate 4-dialkylaminopyridine as an acylation catalyst and a polar aprotic solvent such as acetonitrile (preferred), dimethyl formamide, hexamethyl phosphoramide and the like at temperatures ranging from 40° to 85° C.

Pathway 2 of Scheme VIII depicts the alternative route for introducing an alkoxy-carbonyl-ethyl or $C_{1-2}$alkoxy-$C_{1-2}$alkoxy-carbonyl-ethyl substituent on to the ring nitrogen of (XIV) by the previously described conjugate addition (Michael addition) reaction with an Scheme VIII

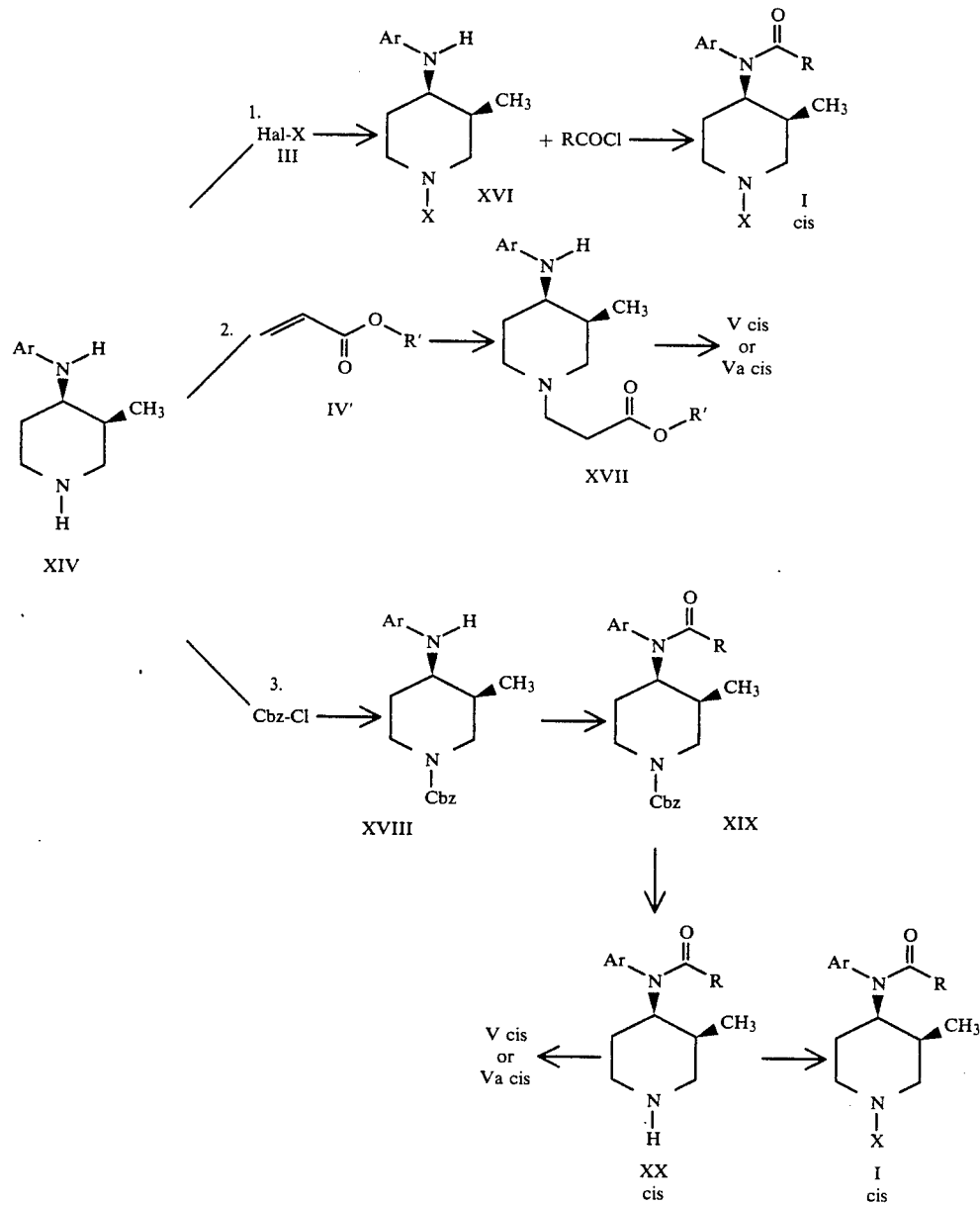

α,β-unsaturated carbonyl reactant of formula (IV') to yield the corresponding cis form of (XVII) which is then acylated with RCOCl as previously described to yield cis product forms of (V) or (V-a). The symbol R' cis final products of formulas (I), (V) or (V-a) by the respective alkylation and Michael additional methodologies previously described using (XX) as the (II) compound.

Scheme IX

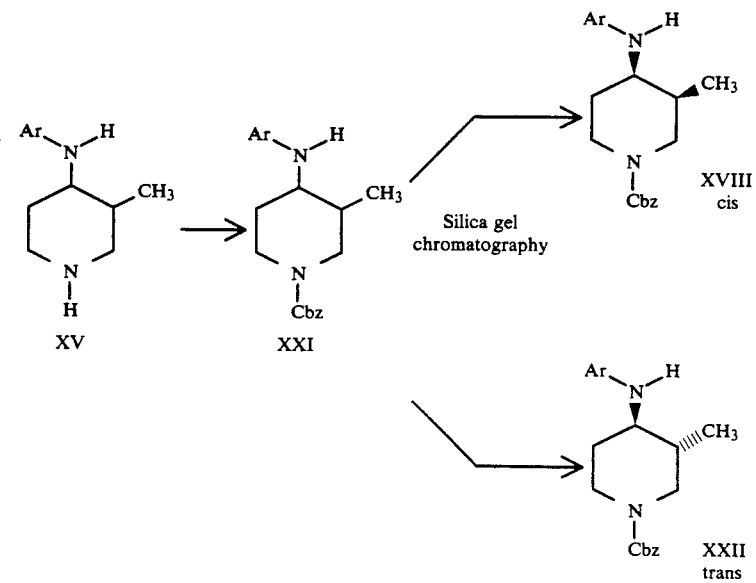

in Scheme VIII represents alkyl, $C_{1-2}$alkoxy-$C_{1-2}$alkyl or alkenyl. By analogy to previous schemes, the acrylic ester of formula (IV') may be substituted by $R^4R^5C=CR^6COOR'$ or alkyl.

Alternative routes for synthesizing cis-(I), cis-(V) and cis-(V-a) are depicted in pathway 2 of Scheme VIII. Reaction of the cis precursor (XIV) with benzylchloroformate (Cbz-Cl) using Schotten-Baumann conditions, two phases consisting of water and an ether, e.g., diethyl ether, tetrahydrofuran, dioxane and the like, in the presence of an appropriate base, e.g., sodium carbonate or bicarbonate, alkali metal (sodium preferred) hydroxide and the like, to scavange the released acid during the reaction, at about 0°-35° C., provides the ring substituted compounds of formula (XVIII), wherein Cbz=benzyloxycarbonyl. Similar acylation of the arylamino group in (XVIII) with RCOCl provides the corresponding amides (XIX). Conventional hydrogenolysis of the benzylcarbamate function of (XIX), for example, with hydrogen at 1-3 atmospheres of pressure in the presence of a catalyst (such as Pd-C) in a mixture of an organic alkanol (such as methanol and ethanol) and acetic acid at ambient temperature provides the cis precursor (XX) wherein the ring nitrogen is unsubstituted. The cis precursor (XX) is then converted to the As indicated in Scheme VII, the trans derivatives (XIII) and (XV) contain some residual corresponding cis isomer. However, final products of formula (I) in pure trans form may be obtained from the trans(cis) derivative (XV) by the purification methodology depicted in Scheme IX. The trans(cis) derivative (XV) is converted to the corresponding trans(cis) N-benzyloxycarbonyl derivative (XXI) under Schotten-Baumann conditions as previously described. The trans(cis) isomers of (XXI) are separable by flash silica gel chromatography (for example, see W. C. Still et al, J. Org. Chem., 1978, 43, 2923) to yield cis (XVIII) and trans (XXII) isomers, each substantially free from the respective corresponding isomeric form. The thus-obtained trans isomers may then be converted to the respective trans form of final products (I) by application of the methodologies heretofore described for the corresponding cis compounds (e.g. pathway 3 of Scheme VIII).

A methodology for synthesizing the corresponding optically isomeric (+) and (−) forms of the pure cis and trans isomers is depicted in Scheme X. For illustration purposes, the racemic cis isomers of formula (XIV) are shown as the starting material, although the corresponding racemic trans isomers can similarly be utilized.

Scheme X

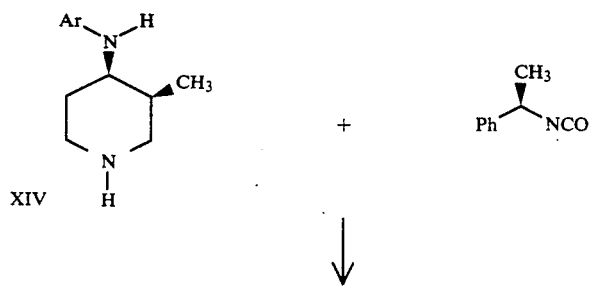

Scheme X

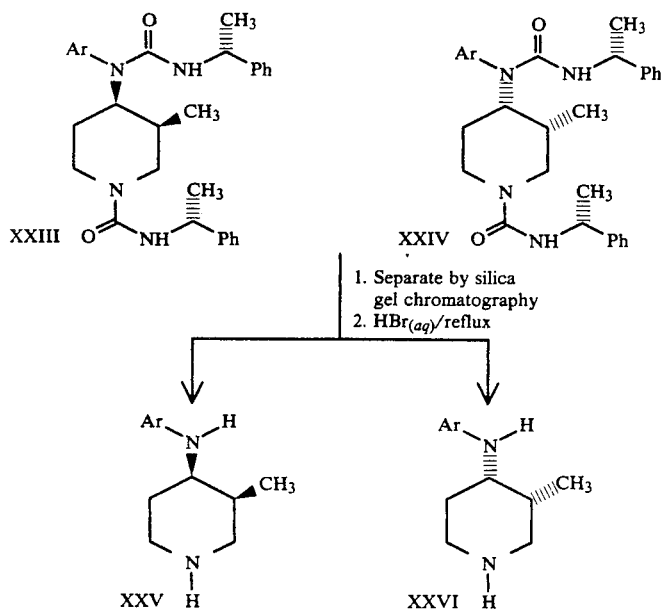

Reaction of racemic cis (XIV) with R-α-methylbenzyl isocyanate at elevated temperatures (about 100°–150° C.) in the presence of an appropriate 4-dialkylaminopyridine catalyst generates the racemic mixture of diastereomeric compounds (XXIII) and (XXIV) which are separable by flash silica gel chromatography. Each of the separated diastereomers are then converted to the respective enantiomeric piperidines (XXV) and (XXVI) by treatment with refluxing hydrobromic acid which, in turn, may then be used as the starting precursor for preparing the corresponding form of the formula (I) compounds in accordance with the previously described methodologies in Scheme VIII.

The compounds of formula (I) and the isomeric forms and pharmaceutically acceptable acid addition salts thereof are useful analgesics, as demonstrated, for example, in experimental animals. Typical of the in vitro and in vivo testing procedures for analgesic activity are the guinea pig ileum assay and the rat tail withdrawal assay, respectively.

A. Guinea Pig Ileum Assay (in vitro)

Compounds are tested for opioid activity in the isolated guinea pig ileum using the method of Kosterlitz, H. W. and Watt, A. J., Br. J. Pharmacol. 33:266–276 (1968) with modifications found in James, M. K. and Leighton, H. J., J. Pharmacol. Exp. Ther. 240:138–144 (1987). The terminal ileum is removed from male Hartley guinea pigs after sacrifice by cervical dislocation. The isolated ileum is washed and placed in Krebs-Henseleit buffer oxygenated with 95% $O_2$ and 5% $CO_2$ mixture and maintained at 37° C. The washed ileum is cut into segments (2.0–2.5 cm) and mounted on platinum ring electrodes. The ileal segments are then placed in 10 ml temperature-controlled tissue baths containing oxygenated Krebs-Henseleit buffer. The tissues are connected to force-disPlacement transducers and stretched to a resting tension of 1.0 gram. The composition of Krebs-Henseleit buffer is as follows (millimolar): NaCl, 118.1; KCl, 4.15; $CaCl_2$, 2.5; $MgSO_4$, 1.2; $KH_2PO_4$, 1.23; $NaHCO_3$, 25.5 and glucose, 11.1.

The ileal segments are stimulated at 0.1 Hertz, 0.5 milliseconds duration at a supramaximal voltage to induce contractions. Opioid activity in the test compounds is manifested as inhibition of electrically evoked contractions. A non-cumulative concentration-effect curve for each test compound is performed to assess the ability of the compound to inhibit contraction in the guinea pig ileum. After the concentration-effect curve is completed, naloxone is added to the tissue baths to determine if the compound-induced inhibition of contraction is reversed. Antagonism of the inhibition by naloxone confirms that the inhibitory effects of the compounds are mediated through opioid receptors. Assay results are expressed as $EC_{50}$ values (a measure of potency), defined as the concentration producing fifty percent of the maximal response, and is expressed in molar units (moles of compound/liter).

B. Rat Tail Withdrawal Assay (in vivo).

The analgesic efficacy of test compounds are evaluated in a rat tail withdrawal reflex model modified from D'Amour, F. E. and Smith D. L., J. Pharmacol. Exp. Ther. 72:74–79 (1941). Male Sprague-Dawley rats are anesthetized and implanted with femoral vein cannulae and allowed to recover overnight. After recovery, the test compounds are administered intravenously through the cannula and effects on tail withdrawal latency are measured. Tail withdrawal latency is measured as the time to tail movement by the rat after exposure of the tail to a radiant heat source. The heat source is calibrated to produce a temperature of 62° C. after 15 seconds. Tail withdrawal latency in the absence of drugs is six to eight seconds. Test compounds demonstrating analgesic activity prolong tail withdrawal latency beyond that seen in the absence of drugs. A maximal latency cut-off of fifteen seconds is imposed to prevent tissue damage. The assay is verified with known opioids as standards. Results of these studies are expressed as $ED_{50}$ values, calculated as the dose producing a tail withdrawal latency equal to half the difference between the maximum latency (15 seconds) and the baseline latency (six to eight seconds). $ED_{50}$ values are expressed as milligrams of compound/kilogram of body weight. Duration of action is defined as the time (in minutes) necessary for the tail withdrawal response to return to baseline values after being elevated in response to drug administration. Duration of action is measured at the lowest dose producing a fifteen second (maximum) tail withdrawal latency.

In Table I, test results obtained from the aforementioned A. guinea pig ileum assay and B. rat tail withdrawal assay are listed for the indicated compounds of formula (I). Said results are not given for the purpose of limiting the invention to said compounds but to exemplify the analgesic activity of all compounds within the scope of formula (I). For comparison purposes, test results obtained for three well known 4-anilidopiperidine analgesics, fentanyl, sufentanil and alfentanil, are also listed.

TABLE I

| Compound of Example | Assay A $EC_{50}$ (molar) | Assay B $ED_{50}$ (mg/kg) | Assay B Duration of Action (min) |
|---|---|---|---|
| 2 maleate | $1.66 \pm 0.59 \times 10^{-6}$ | 3.2 | 10–15 |
| 3 maleate | $3.60 \pm 0.30 \times 10^{-6}$ | 3.4 | 10 |
| 6 HCl | $2.62 \pm 0.62 \times 10^{-6}$ | 4.7 | 5–10 |
| 7 oxalate | $3.71 \pm 0.20 \times 10^{-7}$ | 13.4 | 5–10 |
| 8 oxalate | $1.03 \pm 1.00 \times 10^{-5}$ | — | — |
| 10 oxalate | $3.55 \pm 0.23 \times 10^{-9}$ | 0.0044 | 15 |
| 12 oxalate | $1.02 \pm 0.63 \times 10^{-8}$ | 0.8 | 30 |
| 14 oxalate | $6.89 \pm 1.61 \times 10^{-9}$ | 1.4 | 15 |
| 15 oxalate | $5.11 \pm 0.24 \times 10^{-7}$ | <0.03 | 10 |
| 16 oxalate | $6.72 \pm 2.10 \times 10^{-8}$ | 0.016 | 25 |
| 17 oxalate | $3.47 \pm 0.53 \times 10^{-7}$ | 0.028 | 15 |
| 18 oxalate | $2.13 \pm 0.30 \times 10^{-6}$ | >3.0 | — |
| 19 oxalate | $1.18 \pm 0.20 \times 10^{-7}$ | >3.0 | — |
| 20 oxalate | $4.95 \pm 0.09 \times 10^{-6}$ | 1.4 | 25 |
| 21 oxalate | $2.18 \pm 0.18 \times 10^{-6}$ | 1.4 | 15 |
| 22 HCl | $1.98 \pm 0.21 \times 10^{-8}$ | <0.03 | 30 |
| 23 oxalate | $7.51 \pm 0.81 \times 10^{-8}$ | 0.51 | 10 |
| 24 oxalate | $1.64 \pm 0.10 \times 10^{-8}$ | >3.0 | — |
| 25 oxalate | $1.47 \pm 0.09 \times 10^{-7}$ | 0.052 | 5 |
| 27 HCl | $9.29 \pm 6.36 \times 10^{-9}$ | <0.003 | 10 |
| 29 oxalate | $2.23 \pm 1.00 \times 10^{-8}$ | 0.14 | 10 |
| 34 HCl | $6.63 \pm 1.96 \times 10^{-8}$ | 0.0052 | 10 |
| 35 oxalate | $1.22 \pm 0.09 \times 10^{-8}$ | 0.26 | 20 |
| 36 oxalate | $6.87 \pm 0.83 \times 10^{-9}$ | — | — |
| fentanyl | $1.76 \pm 0.36 \times 10^{-9}$ | 0.0046 | 60 |
| sufentanil | $7.43 \pm 1.53 \times 10^{-9}$ | 0.0013 | 80 |
| alfentanil | $2.01 \pm 0.12 \times 10^{-8}$ | 0.0045 | 55 |

The results in Table I illustrate that the subject compounds have opioid activity as demonstrated by naloxone-reversible inhibition of electrically evoked contraction in the guinea pig ileum. The most preferred compounds are those potent analgesics which also have unexpectedly short durations of action, as compared to known compounds of the 4-anilidopiperidine series (fentanyl, sufentanil and alfentanil). Among the most preferred compounds are:

1. 3-[4-methoxycarbonyl-4-[(1-oxopropyl)-phenylamino]-1-piperidine]propanoic acid, methyl ester (Example 10);
2. 5-4-methoxycarbonyl-4-[(1-oxopropyl)phenylamino]-1-piperidine]pentanoic acid, methyl ester (Example 12);
3. 2-[4-methoxycarbonyl-4-[(1-oxopropyl)-phenylamino]-1-piperidine]ethyl acetate (Example 16);
4. 3-4-(1-oxopropyl)-2-fluorophenylamino]-1-piperidine]-propanoic acid, methyl ester (Example 17);
5. 3-[4-methoxycarbonyl-4-(1-oxopropyl)phenylamino]-1-piperidine]propanoic acid, vinyl ester (Example 15B);

and the pharmaceutically acceptable isomers and salts thereof. A particular group of compounds of the invention are the alkyl esters of 3-4-methoxycarbonyl-4-(1-oxopropyl)-phenylamino-1-piperidine]propanoic acid and their pharmaceutically acceptable salts.

The aforementioned properties of the most preferred compounds are extremely beneficial in that they allow more control over the level of analgesia in a surgical setting or other situation where precise control of opioid levels are necessary or desirable. These properties would also allow for more rapid recovery after the conclusion of a surgical procedure or after the use of these compounds in other circumstances.

In addition, to their analgesic activity, the compounds (I) of this invention may be subject to extensive metabolism in blood as well as potential metabolism in the liver, as has been typically observed with the most preferred compounds. In contrast, fentanyl and alfentanil are reported to be primarily metabolized in the liver in humans, for example, see McClain, D. A. and Hug, Jr., C. C., Clin. Pharm. Ther. 28:106–114 (1980), and Schuttler, J. and Stoeckel, H., Anesthesist 31:10–14 (1982). Rapid elimination or biotransformation to inactive or less active products would minimize accumulation with prolonged or repeated administration. This property has been cited as one of the properties of an "ideal" intravenous analgesic or anesthetic (White, P. F., Anesthesia and Analgesia 68: 161–171 (1989)). In addition, rapid degradation of an opioid analgesic to inactive or less active products in the blood, as occurs with the neuromuscular blocker, succinylcholine, would allow more predictable correlation of dose with duration of pharmacologic effect (Stanski, D. R. and Hug, C. C., Jr. Anesthesiology 57: 435–438 (1982)).

This non-hepatic means of inactivation may be demonstrated with one of the most preferred compounds, 3-[4-methoxycarbonyl-4-[(1-oxo-propyl)phenylamino)-1-piperidine]propanoic acid, methyl ester, as the hydrochloride salt (Test Compound), which is found to be rapidly degraded in rat and human blood in vitro whereas fentanyl, sufentanil and alfentanil are found to degrade at a much slower rate.

The relative assay using rat blood is performed as follows. One hundred microliters of fresh heparinized rat blood is placed in eighteen 15-ml plastic centrifuge tubes. The tubes are then placed in a temperature-controlled water bath at 37 ° C. for 2 minutes. At that time, 2 ug (at a concentration of 1 ug/ml in water) of the Test Compound (12 tubes), fentanyl (2 tubes), sufetanil (2 tubes) and alfentanil (2 tubes) are added to each tube. Two tubes containing the Test Compound are removed at the following times: 0.5, 1.0, 2.0, 5.0, 10.0 and 20.0 minutes. Two tubes each containing the fentanyl, sufentanil and alfentanil are removed after 60 minutes. Immediately after removal from (4-[4-methoxycarbonyl-4-[(1-oxopropyl)phenylamino]-1-piperidine]butanoic acid, methyl ester oxalic acid salt (Example 11) at 0.1 ug/ml in water), the solution briefly mixed, and 900 ul of a saturated solution of sodium carbonate is added. After addition of the sodium carbonate solution, the tube contents are mixed and 10 ml of n-hexane is added.

The aqueous phase is mixed with the n-hexane phase for 10 minutes and centrifuged at 2000 ×g for 10 minutes. The n-hexane layers are removed, placed in clean tubes and evaporated to dryness under a stream of dry nitrogen. To the residue from the evaporation, 100 μl of ethyl acetate is added, mixed and the solution analyzed by gas-liquid chromatography. 1 Microliter aliquots of the ethyl acetate solution are injected into a gas chromatograph fitted with a 0.32 mm (internal diameter)×15 m column coated with DB5 (brand name of J&W Scientific, Rancho Cordoba, Calif. for a 5% diphenylpolysiloxane and 95% dimethylpolysiloxane mixture) to a film thickness of 0.25 μ. The injector port is held at 280° C. The detector is a nitrogen phosphorous detector held at 270° C., and the carrier gas is helium at a flow rate of 2 ml/minute. The column is held at 45° C. for one minute after injection; then heated to 270° C. at a rate of 25° C./minute, and held at 270° C. for seven minutes. Under these conditions, the internal standard has a retention time of 11.6 minutes. The Test Compound, fentanyl, sufentanil and alfentanil have retention times of 11.0, 12.1, 12.8 and 14.3 minutes, respectively.

In this study, it has been found that more than 90% of the Test Compound disappeared after incubation for 30 seconds, whereas 65%. 85% and 75% of the added sufentanil, alfentanil and fentanyl are still present at the end of a one hour incubation period. These results demonstrate that the Test Compound is rapidly degraded in rat blood in vitro in contrast to the three comparative compounds, which degrade at a very slow rate. As a consequence of these findings, the analgesic compounds of this invention may be subject to extensive metabolism in blood as well as potential hepatic metabolism. This property is viewed as advantageous because it offers an alternative means of inactivating the analgesic compound and thereby could produce a predictable pharmacokinetic profile.

Beyond 3-[4-methoxycarbonyl-4-[(1-oxopropyl)-phenylamino]-1-piperidine]propanioc acid, methyl ester this non-hepatic means of inactivation may be demonstrated with the related ethyl, propyl, butyl, isopropyl, isobutyl and sec-butyl esters. These compounds (test compounds below in Table II) have been found to be rapidly degraded in human blood when compared to their degradation in phosphate buffer.

The relative assay using human blood is performed as follows. Twenty ml of fresh, heparinized human blood is placed in a temperature-controlled water bath at 37° C. for 10 minutes. At that time, 400 μl of 2 mg/ml solution of the test compound is added to the blood to give a blood concentration of 40 μg/ml of the test compound. Solutions of the test compounds are prepared just before the assay was started. Two 500 μl of blood are withdrawn at various timepoints for measurement of the test compound and the propanoic acid formed by ester hydrolysis. A trial run was performed with each test compound and thereafter timepoints were set for sampling over two to three half-lives. Chemical hydrolysis is measured by incubating the test compounds in phosphate buffer (0.1 M, pH=7.4) instead of blood. Duplicate samples are taken at 1, 30, 60, 120, 180, 240 and 300 minutes.

Acetonitrile (700 μl) is added to the from the incubation mixture along with 50 μl of a solution of the internal standard (4-[4-methoxycarbonyl-4-[(1-oxopropyl)-phenylamino]-1-piperdine]butanoic acid, methyl ester, 0.12 mg/ml in acetonitrile). Samples are mixed and immediately centrifuged at 30,000 ×g for 10 minutes. The supernatant is removed and cooled to 8° C. Twenty microliters of the supernatant is injected into the high performance liquid chromatograph (HPLC) for analysis.

The HPLC analysis is performed using a 5 μ Spherisorb CN column (250×4.6 mm)(Keystone Scientific, Inc., State College, Pa.) with a flow rate of 2 ml/min. The mobile phase for the assay is 0.1 M phosphate buffer (pH=2.0) and acetonitrile in a gradient elution. Acetonitrile is increased from 10–11% at 0 to 5 minutes to 16% by 10 minutes. Acetonitrile is maintained at 16% through the remainder of the elution (16 minutes inclusive). These conditions provide for resolution of the propanoic acid formed by ester hydrolysis, the internal standard and all of the test compounds except the ethyl ester. Retention times are (in minutes): propanoic acid 5.1; methyl ester 7.5; internal standard 8.6; ethyl ester 9.0; isopropyl ester 11.1; propyl ester 11.8; sec-butyl ester 13.9; iso-butyl ester 14.4.; and butyl ester 14.9.

Slowing the flow rate to 1 ml/minute allows the resolution of the ethyl ester from the internal standard. At this flow rate the retention times are 10.1 minutes for the propanoic acid, 15.1 minutes for the internal standard and 15.8 minutes for the ethyl ester. Elution of these substances is detected by monitoring ultraviolet absorption at a wavelength of 220 nm.

Data from the HPLC assay is analyzed by a simple pseudo-first order kinetic model for disappearance of the test compounds. Pseudo-first order rate constants were calculated for each test compound from these data along with the apparent half-lives in minutes ($t_{\frac{1}{2}}$). These results are shown in Table II below for the various esters of 3-[4-methoxycarbonyl 4-[(1-oxopropyl)-phenylamino]-1-piperidine]propionic acid. Where $k_{Bu}$ is the pseudo-first order rate constant for degradation of the test compounds in phosphate buffer and $k_{Bl}$ is the similar constant for degradation in blood.

TABLE II

| Ester | $k_{Bu}$ | Buffer $t_{\frac{1}{2}}$ | $k_{bl}$ | Blood $t_{\frac{1}{2}}$ |
|---|---|---|---|---|
| methyl | 7.4 ± 0.6 × $10^{-3}$ | 94 | 2.0 ± 0.1 × $10^{-2}$ | 36.5 |
| ethyl | 4.6 ± 0.2 × $10^{-3}$ | 150 | 1.8 ± 0.7 × $10^{-2}$ | 38.5 |
| propyl | 3.0 ± 0.5 × $10^{-3}$ | 231 | 2.5 ± 0.3 × $10^{-2}$ | 27.7 |
| butyl | 3.0 ± 0.5 × $10^{-3}$ | 231 | 8.5 ± 0.6 × $10^{-2}$ | 8.2 |
| isopropyl | 1.3 ± 0.5 × $10^{-3}$ | 533 | 1.0 ± 0.1 × $10^{-2}$ | 69.3 |
| isobutyl | 4.0 ± 0.6 × $10^{-3}$ | 173 | 9.0 ± 2.0 × $10^{-2}$ | 7.7 |
| secbutyl | 2.0 ± 0.2 × $10^{-3}$ | 346 | 9.0 ± 1.0 × $10^{-3}$ | 77.0 |

In this study, it was found that the test compounds were rapidly degraded in blood as compared to buffer. The test compounds were found to be rapidly degraded in human blood in vitro in contrast to the marketed compounds, fentanyl, sufentanil and alfentanil, which have been found to be primarily metabolized in the liver in vivo see D. A. McClain et al, Clin. Pharm. Ther. 28:106–114 (1982). As demonstrated in this study, the analgesic compounds of this invention may be subject to extensive metabolism in blood as well as potential hepatic metabolism. This property is viewed as advantageous because the compounds of this invention would not depend on redistribution for the terminiation of their effects and thereby would likely have a more consistent and predictable pharmacokinetic and pharmacodynamic profile.

In view of their analgesic activity, the subject compounds may be formulated into various pharmaceutical forms for administration purposes. To prepare the pharmaceutical compositions of this invention, an effective analgesic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, for example, for administration orally, transdermally, rectally or parenterally. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. For parenteral compositions, the carrier will usually comprise sterile water, at least in large part, though other ingredients, for example, to aid solubility, may be included. Injectable solutions, for example may be prepared in which the carrier comprises isotonic saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form, as used herein, refers to physically discrete units suitable as unitary dosages, each unit containing a predetermined quantity of active ingredient calculated in product the desired therapeutic effect in association with the required pharmaceutical carrier. Examples of such dosage unit forms are tablets (including scored or coated tablets), capsules, pills, powder packets, wafers, injectable solutions or suspensions, teaspoonsfuls and the like, and segregated multiples thereof.

In view of the analgesic activity of the subject compounds, it is evident that the present invention provides a method of preventing or combatting pain, that is, providing analgesia, in warm-blooded mammals, including humans, by the systemic administration of an effective analgesic amount of a compound of formula (I) or a pharmaceutically acceptable isomer or acid addition salt thereof in admixture with a pharmaceutical carrier. Although the amount of active ingredient to be administered may vary within rather wide limits, depending on the particular circumstances of the case, doses of from about 0.001 to about 10 mg/kg, and preferably from about 0.01 to about 1.0 mg/kg, administered once, repeatedly or continuously (e.g., i.v. drip), are generally found effective. The preferred route of administration is parenteral, particularly by the intravenous route.

The following examples are intended to illustrate, and not to limit the scope of the present invention.

EXAMPLE 1

4-[(1-Oxopropyl)phenylamino]-1-piperidineacetic acid, methyl ester

A mixture of 4-[(1-oxopropyl)phenylamino]-piperidine (500 mg, 2.15 mmol), prepared according to the procedure of P. A. J. Janssen et al, U.S. Pat. No. 3,164,600, methyl bromoacetate (0.25 ml, 2.58 mmol), and potassium carbonate (594 mg, 4.3 mmol), in acetonitrile (2.5 ml) is stirred at room temperature for five hours. The reaction mixture is diluted with 1:1 water and ethyl acetate (20 ml total). The phases are separated and the aqueous phase extracted with ethyl acetate (2×) and the combined organics washed with brine, dried over sodium sulfate and then concentrated. The residue is chromatographed on silica gel (95/5 CHCl$_3$/MeOH) to give 4-[(1-oxopropyl)phenylamino]-1-piperidineacetic acid, methyl ester, as an oil: 348 mg, 53% yield. An equimolar amount of maleic acid in ether is added to a solution of the free base in ethyl acetate to give the maleate salt as a white solid; maleate salt: m.p. 130°–133° C.

| Elemental Analysis for $C_{21}H_{28}N_2O_7$: | | | |
|---|---|---|---|
| | C % | H % | N % |
| Found: | 59.7 | 6.8 | 6.6 |
| Calculated: | 60.0 | 6.7 | 6.7 |

EXAMPLE 2

3-[4-[(1-Oxopropyl)phenylamino]-1-piperidine]-propanoic acid, methyl ester

To a solution of 4-[(1-oxopropyl)phenylamino]-piperidine (1.0 gm, 4.31 mmol) in acetonitrile (10 ml) is added methyl acrylate (776 μl, 8.62 mmol) at room temperature. The solution is stirred at 50° C. for 2 hours, cooled to room temperature and concentrated to an oily residue. The residue is chromatographed on silica gel (EtOAc) to yield 3-[4-[(1-oxopropyl)-phenylamino]-1-piperidine]propanoic acid, methyl ester as an oil: 1.34 gm, 98%. The maleate salt, which is made as described in Example 1 and recrystallized from ethyl acetate, is a white solid; maleate salt: m.p. 118°–120° C.

| Elemental Analysis for $C_{22}H_{28}N_2O_7$: | | | |
|---|---|---|---|
| | C % | H % | N % |
| Found: | 60.8 | 7.0 | 6.7 |
| Calculated: | 60.8 | 7.0 | 6.5 |

EXAMPLE 3

4-[4-[(1-Oxopropyl)phenylamino]-1-piperidine]butanoic acid, methyl ester

A mixture of 4-[(1-oxopropy])phenylamino]-piperidine (250 mg, 1.08 mmol), methyl 4-bromobutanoate (224 mg, 1.23 mmol), prepared according to the procedure of G. A. Olah et al, Synthesis 1982, 963, sodium iodide (81 mg, 0.54 mmol), and potassium carbonate (298 mg, 2.15 mmol), in acetonitrile (1.1 ml) is stirred at room temperature for five hours. The mixture is diluted with water and ethyl acetate and worked up in an analogous manner of Example 1. The residue is chromatographed on silica gel (EtOAc) to give 4-[4-[(1-oxopropyl)phenylamino]-1-piperidine]butanoic acid, methyl ester as an oil: 223 mg, 62%. The maleate salt is made as described in ExamPle 1; maleate salt: m.p. 101.5°–103.5° C.

| Elemental Analysis for $C_{23}H_{32}N_2O_7$: | | | |
|---|---|---|---|
| | C % | H % | N % |
| Found: | 61.3 | 7.0 | 6.2 |

-continued

| Elemental Analysis for $C_{23}H_{32}N_2O_7$: | | | |
|---|---|---|---|
| | C % | H % | N % |
| Calculated: | 61.6 | 7.2 | 6.3 |

EXAMPLE 4

5-[4-[1-Oxopropyl)phenylamino]-1-piperidine]pentanoic acid, methyl ester

A mixture of 4-[(1-oxopropyl)phenylamino]-piperidine (300 mg, 1.29 mmol), methyl-5-bromopentanoate (290 mg, 1.49 mmol), prepared according to the procedure of G. A. Olah et al, Synthesis 1982, 963) sodium iodide (97 mg, 0.65 mmol), and potassium carbonate (357 mg, 2.58 mmol), in acetonitrile (1.3 ml) is stirred at room temperature for five hours. The crude residue is isolated according to the procedure of Example 1. The residue is chromatographed on silica gel (95/5 EtOAc/MeOH) to give 5-[4-[1-oxopropyl) phenylamino]-1-piperidine]pentanoic acid, methyl ester, as a white solid: 239 mg; 53%; m.p. 64°–66° C. The maleate salt is made as described in Example 1; maleate salt: m.p. 105°–106° C.

| Elemental Analysis for $C_{24}H_{34}N_2O_7$: | | | |
|---|---|---|---|
| | C % | H % | N % |
| Found: | 62.3 | 7.4 | 6.0 |
| Calculated: | 62.3 | 7.4 | 6.1 |

EXAMPLE 5

3-[4-[(1-Oxopropyl)phenylamino]-1-piperidine]-propanoic acid, trifluoroacetate

A solution of 4-[(1-oxopropyl])phenylamino]-piperidine (500 mg, 2.15 mmol) and t-butyl acrylate (0.37 ml, 2.58 mmol), in acetonitrile (2.5 ml) is stirred at room temperature for 24 hours. The solution is concentrated and the residue is chromatographed on silica gel (EtOAc) to give 4-[2-[(1-oxopropyl)phenylamino]-1-piperidine propanoic acid, t-butyl ester as an oil: 605 mg, 78%. To the ester (309 mg, 0.857 mmol) is added trifluoroacetic acid (4 ml). The homogeneous reaction mixture is stirred at room temperature for one hour and then concentrated to an oil which is triturated with ether to give a white solid, 3-[4-[(1-oxopropyl)-phenylamino]-1-piperi]-dine]propanoic acid, trifluoroacetate: 316 mg, 88%; m.p. 187°–189° C.

| Elemental Analysis for $C_{19}H_{25}N_2O_5F_3$: | | | |
|---|---|---|---|
| | C % | N % | N % |
| Found: | 54.6 | 6.0 | 6.7 |
| Calculated: | 54.5 | 6.0 | 6.7 |

EXAMPLE 6

A. Methoxymethyl acrylate

In a separatory funnel is added acrylic acid (2 ml, 29.17 mmol), dimethoxymethane (2 ml), phosphorous pentoxide (0.5 g) and ether (20 ml). The mixture is vigorously shaken for five minutes and then an additional aliquot of phosphorous pentoxide is added (0.5 g) and the procedure repeated three times. The solids are separated from the liquid and the ether solution washed with saturated NaHCO₃ solution (3×), then dried over anhydrous Na₂SO₄ and the ether distilled from the product to yield methoxymethyl acrylate as a light yellow oil: 450 mg, 13%.

B. 3-[4-[(1-Oxopropyl)phenylamino]-1-piperidine]-propanoic acid, methoxymethyl ester A solution of 4-[(1-oxopropyl)phenylamino]-piperidine (150 mg, 0.65 mmol) and methoxymethyl acrylate (182 mg, 1.57 mmol), in acetonitrile (0.8 ml) is stirred at room temperature for eleven hours. The solution is evaporated and the residue chromatographed on silica gel (EtOAc) to give 3-[4-[(1-oxopropyl)phenylamino]-1-piperidine]propanoic acid, methoxymethyl ester as an oil: 138 mg, 25%. Gaseous hydrochloric acid is passed through a solution of the free base dissolved in ethyl acetate/ether (¼ ratio) to give the hydrochloride salt as a white solid; HCl salt: m.p. 128°–131° C.

| Elemental Analysis for $C_{19}H_{29}N_2O_4Cl$: | | | |
|---|---|---|---|
| | C % | H % | N % |
| Found: | 59.0 | 7.6 | 7.4 |
| Calculated: | 59.3 | 7.6 | 7.3 |

EXAMPLE 7

2-[4-[(1-Oxopropy))phenylamino]-1-piperidine]ethyl acetate

To a solution of 4-[(1-oxopropyl)phenylamino]-1-piperidineacetic acid, methyl ester (250 mg, 0.82 mmol) in tetrahydrofuran (10 ml) at −78° C. is added lithium aluminum hydride (250 mg, 6.57 mmol) in portions. The suspension is stirred at −78° C. for one hour and then quenched with 2N sodium hydroxide (10 ml). Magnesium sulfate is added to the resulting suspension until it becomes granular. The susPension is then filtered and the filtrate concentrated to a residue. The residue is chromatographed on silica gel (9/1 CHCl₃/CH₃OH) to yield 2-[4-[(1-oxopropyl)phenylamino]-1-piperidine]ethanol as an oil: 155 mg, 68%.

A solution of 2-[4-[(1-oxopropyl)phenylamino]-1-piperidine]ethanol (256 mg, 0.957 mmol), acetic anhydride (0.72 ml, 7.63 mmol), and 4-dimethylaminopyridine (50 mg, 0.41 mmol) in pyridine (5 ml) is stirred at 25° C. for two hours. The solution is concentrated to an oil which is chromatographed on silica gel (EtOAc) to give 2-[4-[(1-oxopropyl)phenylamino]-1-piperidine]ethyl acetate as an oil: 243 mg, 82%. An equimolar amount of oxalic acid is added to a solution of the free base in ethyl acetate. The precipitated salt is recrystallized by adding methanol and heating until the solid goes back into solution. Upon cooling the salt precipitates as a white solid; oxalate salt; m.p. 153°–155° C.

| Elemental Analysis for $C_{20}H_{28}N_2O_7$: | | | |
|---|---|---|---|
| | C % | H % | N % |
| Found: | 58.7 | 6.9 | 6.8 |
| Calculated: | 58.8 | 6.9 | 6.9 |

EXAMPLE 8

3-[4-Methoxymethyl-4-[(1-oxopropyl)phenylamino]-1-piperidine]-propanoic acid, methyl ester A solution of 4-methoxymethyl-4-[(1-oxopropyl)-phenylamino]piperidine (300 mg, 1.0 mmol), prepared by the procedure of P. G. H. Van Daele et al, Arzneim.-Forsch. Drug. Res. 1976, 26, 1521, methyl acrylate (325 μl, 3.61 mmol) and methanol (20 ml) is stirred at 60° C. for 2 hours. The reaction solution is cooled to room temperature and concentrated to an oily residue. The residue is chromatographed on silica gel (9/1 CHCl$_3$/MeOH) to yield 3-[4-methoxy-methyl-4-[(1-oxopropyl)phenylamino]-1-piperidine]propanoic acid, methyl ester as an oil: 250 mg, 64%. The oxalate salt is made as described in Example 7; oxalate salt: m.p. 180°–182° C.

| Elemental Analysis for $C_{22}H_{32}N_2O_8$: | | | |
|---|---|---|---|
| | C % | H % | N % |
| Found: | 58.2 | 7.2 | 6.1 |
| Calculated: | 58.4 | 7.1 | 6.2 |

EXAMPLE 9

4-Methoxycarbonyl-4-[(1-oxopropyl)phenylamino]-1-piperidineacetic acid methyl ester A mixture of 4-methoxycarbonyl-4-[(1-oxopropyl])-phenylamino]piperidine (200 mg, 0.68 mmol), prepared according to the procedure of P. G. H. Van Daele et al, Arzneim.-Forsch. Drug Res. 1976, 26, 1521, methyl bromoacetate (200 μl, 2.11 mmol), and potassium carbonate (200 mg, 5.3 mmol), in acetonitrile (1.1 ml) is stirred at room temperature for 2 hours. The reaction mixture is concentrated and chromatographed on silica gel (95/5 CHCl$_3$/MeOH) to yield 4-methoxycarbonyl-4-[(1-oxopropyl)phenylamino]-1-piperidineacetic acid, methyl ester as an oil: 142 mg, 57%. The oxalate salt is made as described in Example 7; oxalate salt m.p. 130°–135° C.

| Elemental Analysis for $C_{21}H_{28}N_2O_9$: | | | |
|---|---|---|---|
| | C % | H % | N % |
| Found: | 55.3 | 6.1 | 6.1 |
| Calculated: | 55.8 | 6.2 | 6.2 |

EXAMPLE 10

3-[4-Methoxycarbonyl-4-[(1-oxopropyl)phenylamino]-1-piperidine]propanoic acid, methyl ester To a solution of 4-methoxycarbonyl-4-[(1-oxopropyl)phenylamino]-piperidine (200 mg, 0.68 mmol) in acetonitrile (1.1 ml) is added methyl acrylate (124 μl, 1.36 mmol) at room temperature. The solution is stirred at 50° C. for 2 hours, cooled to room temperature, and concentrated to an oily residue. The residue is chromatographed on silica gel (EtOAc) to give 3-[4-methoxycarbonyl-4-[(1-oxopropyl)phenylamino]-1-piperidine]propanoic acid, methyl ester as an oil: 253 mg, 97%. The oxalate salt, which is made as described in Example 7 is recrystallized from methanol and 2-butanone; oxalate salt: m.p. 170°–172° C.

| Elemental Analysis for $C_{22}H_{30}N_2O_9$: | | | |
|---|---|---|---|
| | C % | H % | N % |
| Found: | 56.5 | 6.5 | 6.0 |
| Calculated: | 56.7 | 6.4 | 6.0 |

EXAMPLE 11

4-[4-Methoxycarbonyl-4-[(1-oxopropyl)phenylamino]-1-piperidine]-butanoic acid, methyl ester A mixture of 4-methoxycarbonyl-4-[(1-oxopropyl)-phenylamino]-piperidine (150 mg, 0.517 mmol), methyl 4-bromobutanoate (187 mg, 1 mmol), potassium carbonate (39.3 mg, 1 mmol), sodium iodide (155 mg, 1.0 mmol) and acetonitrile (1 ml) is stirred at 50° C. for 2 hours. The mixture is cooled to room temperature, diluted with ethyl acetate (1 ml) and filtered. The filtrate is concentrated to an oily residue which is chromatographed on silica gel (9/1 CHCl$_3$/MeOH) to yield 4-[4-methoxycarbonyl-4-[(1-oxopropyl)phenylamino]-1-piperidine]butanoic acid, methyl ester as an oil: 177 mg, 88%. The oxalate salt is made as described in Example 7; oxalate salt: m.p. 153°–155 C.

| Elemental Analysis for $C_{23}H_{32}N_2O_9$: | | | |
|---|---|---|---|
| | C % | H % | N % |
| Found: | 57.1 | 6.6 | 5.8 |
| Calculated: | 57.5 | 6.7 | 5.8 |

EXAMPLE 12

5-[4-Methoxycarbonyl-4-[(1-oxopropyl)phenylamino]-1-piperidine]pentanoic acid, methyl ester A mixture of 4-methoxycarbonyl-4-(1-oxopropyl)-phenylamino]piperidine (150 mg, 0.517 mmol) methyl 5-bromopentanoate (200 mg, 1 mmol), potassium carbonate (40 mg, 1 mmol), sodium iodide (1.55 mg, 1 mmol) and acetonitrile (1.0 ml) is stirred at 52° C. for 22.5 hours and then at 25° C. for 12 hours. The reaction mixture is diluted with ethyl acetate (1 ml) and filtered. The filtrate is concentrated to an oily residue which is chromatographed on silica gel (90/9/1 CHCl$_3$/MeOH/triethylamine) to yield 5-[4-methoxycarbonyl-4-[(1-oxopropyl)phenylamino-]1-piperidine]-pentanoic acid, methyl ester as an oil: 184 mg, 88%. The oxalate salt is made as described in Example 7; oxalate salt: m.p. 164°–166° C.

| Elemental Analysis for $C_{24}H_{34}N_2O_9$: | | | |
|---|---|---|---|
| | C % | H % | N % |
| Found: | 58.0 | 7.0 | 5.7 |
| Calculated: | 58.3 | 7.0 | 5.7 |

EXAMPLE 13

3-[4-Methoxycarbonyl-4-[(1-oxopropyl)phenylamino]-1-piperidine]propanoic acid, trifluoroacetate This compound is by following the procedure of Example 5 except that an equivalent amount of 4-methoxycarbonyl-4-[(1-oxopropyl)phenylamino]-piperidine is substituted for the 4-[(1-oxopropyl)- phenylamino]-piperidine used therein; m.p. 189°–190° C.

Elemental Analysis for $C_{21}H_{27}N_2O_7F_3$:

|  | C % | H % | N % |
|---|---|---|---|
| Found: | 53.0 | 5.7 | 5.9 |
| Calculated: | 52.9 | 5.7 | 5.9 |

EXAMPLE 14

3-[4-Methoxycarbonyl-4-[(1-oxopropyl)phenylamino]-1-piperidine]-propanoic acid, methoxymethyl ester A solution of 4-methoxycarbonyl-4-[(1-oxopropyl)-phenylamino]piperidine (200 mg, 0.69 mmol) and methoxymethyl acrylate (120 mg, 1.03 mmol) in acetonitrile (0.7 ml) is stirred at room temperature for fifteen hours. The solution is diluted with 1:1 water and ethyl acetate and the aqueous phase extracted with ethyl acetate (2×). The combined organics are washed with brine, dried over sodium sulfate and concentrated. The residue is chromatographed on silica gel (EtOAc) to give 3-[4-methoxycarbonyl-4-[(1-oxopropyl)-phenylamino]-1-piperidine]propanoic acid, methoxymethyl ester as an oil: 160 mg, 57%. The oxalate salt is made as described in Example 7; oxalate salt: m.p. 141°–143° C.

Elemental Analysis for $C_{23}H_{32}N_2O_{10}$:

|  | C % | H % | N % |
|---|---|---|---|
| Found: | 55.4 | 6.5 | 5.5 |
| Calculated: | 55.6 | 6.5 | 5.6 |

EXAMPLE 15

A. Vinyl 3-bromopropionate

This compound is prepared according to the procedure of R. L. Adelman, J. Org. Chem. 1949, 1057. To a solution of 3-bromo-propionic acid (1.0 g, 6.54 mmol) in vinyl acetate (3.6 ml) is added copper (100 mg), mercuric acetate (104 mg) and concentrated sulphuric acid (1 drop) in that order. The reaction is stirred at room temperature for two days. The heterogeneous mixture is diluted with pentane (10 ml) and then filtered through celite to remove the solids. The filtrate is washed with water (2×), saturated sodium bicarbonate (1×) and then brine. The organics are dried over anbychrous sodium sulfate and concentrated to an oil, vinyl 3-bromopropionate: 760 mg, 65%.

B.
3-[4-Methoxycarbonyl-4-[(1-oxopropyl)phenylamino]-1-piperidine]propanoic acid, vinyl ester A mixture of 4-methoxycarbonyl-4-[(1-oxopropyl)-phenylamino]piperidine (200 mg, 0.689 mmol), vinyl 3-bromopropionate (185 mg, 1.03 mmol), and potassium carbonate (214 mg, 1.55 mmol), in acetonitrile (1 ml) is stirred at room temperature for two hours. The reaction mixture is diluted with 1:1 water and ethyl acetate and extracted with ethyl acetate (2×). The combined organics are washed with brine, dried over sodium sulfate and concentrated. The residue is chromatographed on silica gel (EtOAc) to yield 3-[4-methoxycarbonyl-4-[(1-oxopropyl)phenylamino]-1-piperidine]propanoic acid, vinyl ester as a white solid: 197 mg, 74%, m.p. 70°–72°

C. The oxalate salt is made as described in Example 7; oxalate salt: m.p. 156°–158° C.

Elemental Analysis for $C_{23}H_{30}N_2O_9$:

|  | C % | H % | N % |
|---|---|---|---|
| Found: | 57.6 | 6.4 | 5.9 |
| Calculated: | 57.7 | 6.3 | 5.9 |

EXAMPLE 16

2-[4-Methoxycarbonyl-4-[(1-oxopropyl)phenylamino]-1-piperidine]-ethyl acetate

A mixture of 4-methoxycarbonyl-4-[(1-oxopropyl)-phenylamino]piperidine (300 mg, 1.0 mmol), 2-bromoethyl acetate (172 mg, 1.0 mmol), potassium carbonate (79 mg, 2.0 mmol), sodium iodide (154 mg, 1.0 mmol) and acetonitrile (1.0 ml) is stirred at 65° C. for 12 hours, cooled to room temperature, and filtered. The filtrate is concentrated to an oily residue which is chromatographed on silica gel (EtOAc) to yield 2-[4-methoxycarbonyl-4-[(1-oxopropyl)phenylamino]-1-piperidine]ethyl acetate as a yellow oil: 300 mg, 77%. The oxalate salt is made as described in Example 7; oxalate salt: m.p. 191°–193° C.

Elemental Analysis for $C_{22}H_{30}N_2O_9$:

|  | C % | H % | N % |
|---|---|---|---|
| Found: | 56.6 | 6.5 | 6.0 |
| Calculated: | 56.6 | 6.5 | 6.0 |

EXAMPLE 17

3-[4-[(1-Oxopropyl)-2-fluorophenylamino]-1-piperidine]propanoic acid, methyl ester A mixture of 4-[(1-oxopropyl)-2-fluorophenylamino]-piperidine (200 mg, 0.80 mmol), methyl acrylate (0.1 ml, 1.12 mmol) and potassium carbonate (275 mg, 2.0 mmol) in methanol (2 ml) is stirred at room temperature for two hours. The reaction mixture is diluted with 1:1 water and ethyl acetate. After extracting the aqueous phase with ethyl acetate (2×) the combined organics are washed with brine, then dried over sodium sulfate and concentrated. The residue is chromatographed on silica gel (EtOAc) to give 3-[4-[(1-oxopropyl)-2-fluorophenylamino]-1-piperidine]propanoic acid, methyl ester as an oil which solidifies upon standing: 176 mg, 65%. The oxalate salt is made as described in Example 7; oxalate salt: m.p. 183°–184° C.

Elemental Analysis for $C_{20}H_{27}N_2O_7F$:

|  | C % | H % | N % |
|---|---|---|---|
| Found: | 55.9 | 6.4 | 6.5 |
| Calculated: | 56.3 | 6.4 | 6.6 |

EXAMPLE 18

3-[(4-[1-Oxopropyl)-2-fluorophenylamino]-1-piperidine]propanoic acid, vinyl ester By following the procedure in Example 15, except that an equivalent amount of 4-[(1-oxopropyl)-2-fluorophenylamino]piperidine is substituted for the 4-methoxycarbonyl-4-[(1-oxopropyl)phenylamino]-piperidine used therein and the reaction mixture is stirred for sixteen hours, there is obtained 3-[4-[(1-oxopropyl)-2-fluorophenylamino]-1-piperipine]propanoic acid vinyl ester as an oil: 66% yield. The oxalate salt is made as described in Example 7; oxalate salt: m.p. 141°–143° C.

| Elemental Analysis for $C_{21}H_{27}N_2O_7F$: | | | |
|---|---|---|---|
| | C % | H % | N % |
| Found: | 57.6 | 6.2 | 6.4 |
| Calculated: | 57.5 | 6.2 | 6.4 |

EXAMPLE 19

3-[4-[(1-Oxopropyl)-2-fluorophenylamino]-1-piperidine]propanoic acid, 3-butenyl ester A solution of 3-[4-[(1-oxopropyl)phenylamino]-1-piperidine]propanoic acid, trifluoroacetate (370 mg, 0.848 mmol), m.p. 139.5°–141° C., is prepared in an analogous manner in which 3-[4-[(1-oxopropyl)-phenylamino]-1-piperidine]propanoic acid, trifluoroaetate is described in example 5, is dissolved in a 1M phosphate buffer solution (0.5M $Na_2HPO_4$ and 0.5M $Na_2HPO_4$) and stirred for ten minutes. The solution is then diluted with a 3/1 mixture of chloroform/isopropanol and extracted (5×). The combined organics are dried over sodium sulfate and concentrated to the free base: 215 mg, 79% yield. A solution of 3-[4-[(1-oxopropyl)-2-fluorophenyl-amino]-1-piperidine]propanoic acid (185 mg, 0.574 mmol) in chloroform (5 ml) is added O-3-butenyl-N,N-diisopropylpseudo urea (570 mg, 2.87 mmol), prepared using the procedure given in L. J. Mathias, Synthesis, 1979, 561. The solution is refluxed for 24 hours, cooled, and concentrated. The residue is chromatographed on silica gel (1/1 hexanes/EtOAc) to give 3-[4-(1-oxopropyl)-2-fluorophenylamino-1-piperidine]propanoic acid, 3-butenyl ester as an oil: 120 mg, 56%. The oxalate salt is made as described in example 7; oxalate salt: m.p. 165.5°–166.5° C.;

| Elemental Analysis for $C_{23}H_{31}N_2O_7F$: | | | |
|---|---|---|---|
| | C % | H % | N % |
| Found: | 58.8 | 6.8 | 6.0 |
| Calculated: | 59.2 | 6.7 | 6.0 |

EXAMPLE 20

3-[4-[(2-Methoxy-1-oxoethyl)phenylamino]-1-piperidine]propanoic acid, methyl ester A solution of 4-[(2-methoxy-1-oxoethyl)-phenylamino]piperidine (200 mg, 0.805 mmol), prepared according to the procedures of B. S. Huang et al, U.S. Pat. No. 4,584,303, and methyl acrylate (94 µl, 1.05 mmol), in methanol (1 ml) is stirred at room temperature for four hours. The reaction solution is concentrated to a residue which is chromatographed on silica gel (95/5 $CHCl_3$/MeOH) to give the free base, 3-[4-[(2-methoxy-1-oxoethyl)phenylamino]-1-piperidine]-propanoic acid, methyl ester, as an oil: 260 mg, 97%. An equimolar amount of oxalic acid in ether is added to a solution of the free base in ether. The gummy precipitate is triturated with ethyl acetate to give the oxalate salt as a white solid; oxalate salt: m.p. 188°–190° C.

| Elemental Analysis for $C_{20}H_{28}N_2O_8$: | | | |
|---|---|---|---|
| | C % | H % | N % |
| Found: | 56.6 | 6.7 | 6.6 |
| Calculated: | 56.6 | 6.7 | 6.6 |

EXAMPLE 21

3-[4-[(2-Methoxy-1-oxoethyl)-2-fluorophenylamino]-1-piperidine]propanoic acid methyl ester A solution of 4-[(2-methoxy-1-oxoethyl)-2-fluorophenylamino]piperidine (250 mg, 0.94 mmol), methyl acrylate (170 µl, 1.88 mmol) and methanol (5.0 ml) is stirred at room temperature for 24 hours. The reaction solution is concentrated to an oily residue and chromatographed on silica gel (EtOAc) to yield 3-[4-[(2-methoxy-1-oxoethyl)-2-fluorophenylamino]-1-piperidine]propanoic acid, methyl ester as an oil: 202 mg, 61%. The oxalate salt is made as described in Example 7; oxalate salt: m.p. 186°–188° C.

| Elemental Analysis for $C_{20}H_{27}N_2O_8F$: | | | |
|---|---|---|---|
| | C % | H % | N % |
| Found: | 54.3 | 6.1 | 6.4 |
| Calculated: | 54.3 | 6.2 | 6.3 |

EXAMPLE 22

[±]-Cis-3-[3-methyl-4-(1-oxopropyl)phenylamino]-1-piperidine]propanoic acid, methyl ester A solution of (±)-cis-3-methyl-4-phenylaminopiperidine (750 mg, 3.94 mmol), prepared according to the procedure of W. F. M. Van Bever et al., J. Med. Chem. 1974, 17, 1047, methyl acrylate (710 µl, 7.88 mmol), and methanol (2.5 ml) is stirred at room temperature for 30 minutes. The resultant solution is concentrated to an oily residue which is chromatographed on silica gel (EtOAc) to yield (±)-cis-3-(3-methyl-4-phenylamino-1-piperidine)propanoic acid, methyl ester as an oil: 787 mg, 72%.

A solution of (±)-cis-3-(3-methyl-4-phenylamino-1piperidine)-propanoic acid, methyl ester (500 mg, 1.8 mmol), propionyl chloride (785 µl, 9.0 mmol), and 4-dimethylaminopyridine (320 mg, 2.63 mmol) in acetonitrile (10 ml) is stirred and refluxed for 30 minutes. The resultant solution is cooled to room temperature and diluted with cold saturated ethyl acetate (2×25 ml) and the organic phase dried over magnesium sulfate and concentrated to an oily residue which is chromatographed on silica gel (EtOAc) to give (±)-cis-3-[3-methyl-4-[(3-oxopropyl)phenylamino]-1-piperidine]-propanoic acid, methyl ester as an oil: 392 mg, 65%. The hydrochloride salt is made by dissolving the free base in toluene, saturating the solution with dry hydrogen chloride and concentrating to a solid. The solid is then recrystallized from ethyl acetate; hydrochloride salt: m.p. 180°–187° C.

| Elemental Analysis for $C_{19}H_{29}N_2O_3Cl$: | | | |
|---|---|---|---|
| | C % | H % | N % |
| Found: | 61.5 | 7.9 | 7.9 |
| Calculated: | 61.9 | 7.9 | 7.6 |

EXAMPLE 23

[±]-Cis-3-[3-methyl-4-(1-oxopropyl)phenylamino]-1-piperidine]propanoic acid, methoxymethyl ester A mixture of (±)-cis-3-methyl-4-phenylaminopiperidine (350 mg, 1.8 mmol), 2-bromopropanoic acid methoxymethyl ester (450 mg, 2.28 mmol), potassium carbonate (350 mg, 2.54 mmol), 4-dimethyl-aminopyridine (50 mg, 0.41 mmol), and acetonitrile (3 ml) is stirred at room temperature for 24 hours and diluted with saturated sodium bicarbonate (20 ml). The resultant mixture is extracted with ethyl acetate (2×20 ml) and the organic phases combined, dried over magnesium sulfate, and concentrated to an oily residue which is chromatographed on silica gel (EtOAc) to give (±)-cis-3-(3-methyl-4-phenylamino-1-piperidine)propanoic acid, methoxymethyl ester as an oil: 371 mg; 66%.

A solution of (±)-cis-3-(3-methyl-4-phenylamino-1-piperidine)propanoic acid, methoxymethyl ester (350 mg, 1.14 mmol), 4-dimethyl-aminopyridine (250 mg, 2.0 mmol), propionyl chloride (1.0 ml, 11.5 mmol), and acetonitrile (10 ml) is stirred and refluxed for 30 minutes and cooled to room temperature. The reaction solution is diluted with cold saturated sodium carbonate solution (25 ml) and extracted with ethyl acetate (3×25 ml). The organic extracts are combined, dried over magnesium sulfate and concentrated to an oily residue which is chromatographed on silica gel (1/1 EtOAc/Hex) to give (±)-cis-3-[3-methyl-4-[(1-oxopropyl)-phenylamino]-1-piperidine]propanoic acid, methoxymethyl ester as an oil: 253 mg, 60%. The oxalate salt hemihydrate is made as described in Example 7; oxalate salt hemihydrate: m.p. 83°–92° C.

| Elemental Analysis for $C_{22}H_{32}N_2O_8 \cdot 0.5\ H_2O$: | | | |
|---|---|---|---|
| | C % | H % | N % |
| Found: | 57.4 | 7.2 | 6.2 |
| Calculated: | 57.3 | 7.2 | 6.1 |

EXAMPLE 24

[±]-Cis-3-[3-methyl-4-(1-oxopropyl)phenylamino]-1-piperidine]propanoic acid, allyl ester A solution of (±)-cis-3-methyl-4-phenylamino piperidine (400 mg, 2.1 mmol), allyl acrylate (471 mg, 4.2 mmol), and acetonitrile (5 ml) is stirred at room temperature for 4 hours and concentrated to an oily residue which is chromatographed on silica gel (EtOAc) to give (±)-cis-3-[3-methyl-4-phenylamino-1-piperidine]-propanoic acid, allyl ester as an oil: 405 mg; 64%.

A solution of (±)-cis-3-(3-methyl-4-phenylamino-1-piperidine)propanoic acid, allyl ester (400 mg, 1.32 mmol), 4-dimethylaminopyridine (250 mg, 2.0 mmol), propionyl chloride (1.15 ml, 13.2 mmol), and acetonitrile (10 ml) is stirred and refluxed for 30 minutes and cooled to room temperature. The reaction solution is diluted with a solution of cold saturated sodium carbonate (25 ml) and extracted with ethyl acetate (3×25 ml). The organic extracts are combined, dried over magnesium sulfate, and concentrated to an oily residue which is chromatographed on silica gel (1/1 EtOAc/Hex) to give (±)-cis-3-[3-methyl-4-[(1-oxopropyl)-phenylamino]-1-piperidine]propanoic acid, allyl ester as an oil: 335 mg; 74%. The oxalate salt is made as described in Example 7; oxalate salt: m.p. 150°–152° C.

| Anal Calcd. for $C_{23}H_{32}N_2O_7$: | | | |
|---|---|---|---|
| | C % | H % | N % |
| Found: | 61.6 | 7.2 | 6.3 |
| Calculated: | 61.6 | 7.2 | 6.3 |

EXAMPLE 25

[±]-Cis-2-[3-methyl-4-[(1-oxopropyl)phenylamino]-1-piperidine]ethyl acetate

A mixture of (±)-cis-3-methyl-4-phenylaminopiperidine (300 mg, 1.57 mmol), bromoethyl acetate (865 μl, 789 mmol), 4-dimethyl-aminopyridine (100 mg, 0.82 mmol), potassium carbonate (250 mg, 1.81 mmol), and acetonitrile (4 ml) is stirred at room temperature for 6 hours. The resultant mixture is diluted with water (25 ml) and extracted with ethyl acetate (3×25 ml). The combined organic phases are dried over magnesium sulfate and concentrated to an oily residue which is chromatographed on silica gel (3/1 EtOAc/Hex) to give (±)-cis-2-(3-methyl-4-phenylamino-1-piperidine)ethyl acetate as an oil: 402 mg, 92%.

A solution of (±)-cis-2-(3-methyl-4-phenylamino-1-piperidine)ethyl acetate (400 mg, 1.45 mmol), propionyl chloride (1.25 ml, 14.5 mmol), 4-dimethylaminopyridine (353 mg, 2.89 mmol), and acetonitrile (10 ml) is stirred and refluxed for 30 minutes. The resultant solution is cooled to room temperature and diluted with a cold saturated sodium carbonate solution (3×25 ml) and the organic phase over magnesium sulfate and concentrated to an oily residue which is chromatographed on silica gel (EtOAc) to give (±)-cis-2-[3-methyl-4-[(1-oxopropyl)phenylamino]-1-piperidine]ethyl acetate as an oil: 389 mg, 81%. The oxalate salt is made as described in Example 7; oxalate salt: m.p. 148°–150° C.

| Elemental Analysis for $C_{21}H_{30}N_2O_7$: | | | |
|---|---|---|---|
| | C % | H % | N % |
| Found: | 59.6 | 7.3 | 6.6 |
| Calculated: | 59.7 | 7.2 | 6.6 |

EXAMPLE 26

(−)-Cis-3S-methyl-4R-(N-1R-methylbenzylamido)-phenylamino]-1-(N-1R-methylbenzylamido)piperidine and (−)-cis-3R-methyl-4S-(N-1R-methylbenzylamido)-phenylamino]-1-(N-1R-methylbenzylamido)piperidine A solution of (±)-cis-3-methyl-4-phenylaminopiperidine (2.0 gm, 10.5 mmol), 4-dimethylaminopyridine (250 mg, 2.0 mmol), and R-(+)-α-methylbenzyl isocyanate (4.0 gm, 27.2 mmol) is stirred at 120° for 6 hours. The resultant solution is cooled to room temperature and chromatographed on silica gel (1/1 EtOAc/Hex) to give two diastereomers. The less polar of the two is recrystallized from EtOAc to give (−)-cis-3S-methyl-4R-[(N-1R-methylbenzylamido)phenylamino]-1-(N-1R-methylbenzylamido)piperidine as a solid: 1.5 gm; m.p. 172°–173° C.; $[\alpha]_D^{25} = -114.4°$ (c 1.5, MeOH).

| Elemental Analysis for $C_{30}H_{36}N_3O_2$: | | | |
|---|---|---|---|
| | C % | H % | N % |
| Found: | 74.4 | 7.5 | 11.6 |

-continued

| Elemental Analysis for $C_{30}H_{36}N_3O_2$: | | | |
|---|---|---|---|
| | C % | H % | N % |
| Calculated: | 74.4 | 7.5 | 11.6 |

The more polar diastereomer is recrystallized from EtOAc/Hex to give (−)-cis-3R-methyl-4S-[(N-1R-methyl-benzylamido)phenylamino]-1-(N-1R-methyl-benzylamido)-piperidine as a solid: 1.8 gm; m.p. 105°–106° C.; $[\alpha]_D^{25} = -63.6°$ (c 1.8, MeOH).

EXAMPLE 27

[−]-Cis-3-3R-methyl-4S-(1-oxopropyl)phenylamino]-1-piperidine]propanoic acid, methyl ester A suspension of (−)-cis-3R-methyl-4S-(N-1R-methylbenzyl-amido)phenylamino]-1-(N-1R-methylbenzylamido)piperidine (1.75 gm, 3.6 mmol) in 48% hydrobromic acid (40 ml) is stirred and refluxed for 24 hours. It is cooled and concentrated to an oil which is dissolved in water (20 ml) and extracted with ether (2×50 ml). The aqueous phase is basified to pH 10.5 with 5N NaOH and extracted with ethyl acetate (2×25 ml). The ethyl acetate extracts are combined, dried over magnesium sulfate, and concentrated to give a solid which is recrystallized from EtOAc/Hex giving (+)-cis-3R-methyl-4S-phenylaminopiperidine as a solid: 610 mg; 89%; m.p. 95°–97° C.; $[\alpha]_D^{25} = 7.5°$ (c 2.5, MeOH).

A solution of (+)-cis-3R-methyl-4S-phenylaminopiperidine (500 mg, 2.63 mmol), methyl acrylate (473 µl 5.26 mmol), and methanol (10 ml) is stirred at room temperature for 6 hours and concentrated to an oily residue which is chromatographed on silica gel (EtOAc) to give (+)-cis-3-(3R-methyl-4S-phenylamino-1-piperidine)propanoic acid, methyl ester as an oil: 623 mg; 86%; $[\alpha]_D^{25} = +25.7°$ (c 1.85, MeOH).

A solution of (+)-cis-3-(3R-methyl-4S-phenylamino-1-piperidine)propanoic acid, methyl ester (600 mg, 2.17 mmol), 4-dimethylaminopyridine (250 mg, 2.05 mmol), propionyl chloride (1.89 ml, 21.7 mmol), and acetonitrile (10 ml) is stirred and refluxed for 30 minutes and cooled to room temperature. It is diluted with cold saturated sodium carbonate (50 ml) and extracted with ethyl acetate (3×25 ml). The extracts are dried over magnesium sulfate and concentrated to an oily residue which is chromatographed on silica gel (1/1 EtOAc/Hex) to give (−)-cis-3-[3R-methyl-4S-[(1-oxopropyl)-phenyl-amino]-1-piperidine]propanoic acid, methyl ester as an oil: 453 mg; 63%; $[\alpha]_D^{25} = -3.2°$ (c 1.5, MeOH). The hydrochloride salt is made as described in Example 22; hydrochloride salt: m.p 151°–152° C.;

| Elemental Analysis for $C_{19}H_{29}N_2O_3Cl$: | | | |
|---|---|---|---|
| | C % | H % | N % |
| Found: | 62.2 | 7.9 | 7.8 |
| Calculated: | 61.9 | 7.9 | 7.6 |

EXAMPLE 28

Trans-3-methyl-4-[(1-oxopropyl)phenylamino]-piperidine

A mixture of cis and trans-3-methyl-4-phenylaminopiperidine (1.2 g, 6.35 mmol) (predominantly trans due to isolation of the pure cis isomer by crystallization), prepared according to the procedure of W. F. M. Van Berer et al., J. Med. Chem. 1974, 17, 1047 and T. R. Burke, Jr. et al., J. Med. Chem. 1986, 29, 1087, benzylchloroformate (1 ml, 6.98 mmol), sodium bicarbonate (1 g, 11.8 mmol), ether (5 ml), ethyl acetate (5 ml), and water (10 ml) is vigorously stirred at room temperature for one hour. The organic layer is separated, washed with 2N NaOH (2×5 ml), dried over magnesium sulfate, and concentrated to an oily residue which is chromatographed on silica gel (EtOAc) to give trans-N-benzyloxycarbonyl-3-methyl-4-phenylaminopiperidine as an oil: 1.82 g; 91%, followed by less than 5% of cis-N-benzyloxycarbonyl-3-methyl-4-phenylaminopiperidine.

To a solution of trans-N-benzyloxycarbonyl-3-methyl-4-phenylaminopiperidine (1.5 g, 4.6 mmol), 4-dimethylaminopyridine (375 mg, 3.1 mmol), and acetonitrile (10 ml) is added propionyl chloride (3.6 ml, 41 mmol). The solution is stirred and refluxed for 30 minutes, cooled to room temperature, and diluted with a saturated solution of sodium carbonate (30 ml). The resultant mixture is extracted with ethyl acetate (2×30 ml) and the organic phases combined, dried over magnesium sulfate, and concentrated to an oily residue which is chromatographed on silica gel (1/1 EtOAc/Hex) to give trans-N-benzyloxycarbonyl-3-methyl-4-[(1-oxopropyl)-phenylamino]piperidine as an oil: 1.6 g, 91%.

A mixture of trans-N-benzyloxycarbonyl-3-methyl-4-[(1-oxopropyl)phenylamino]-piperidine (1.5 g, 3.94 mmol), 10% Pd-C (200 mg), methanol (20 ml), and acetic acid (20 ml) is hydrogenated at 50 psi for 24 hours. The resultant suspension is filtered through a bed of Celite and the filtrate concentrated. The residue is diluted with ethyl acetate (50 ml), basified to pH 11 with 2N NaOH and shaken. The organic layer is separated, dried over magnesium sulfate, and concentrated to trans-3-methyl-4-[(1-oxopropyl)-phenylamino]-piperidine: 720 mg; 96%.

EXAMPLE 29

Trans-3-[3-methyl-4-[(1-oxopropyl)phenylamino]-piperidine]propanoic acid, methyl ester A solution of trans-3-methyl-4-[(1-oxopropyl)-phenylamino]-piperidine (250 mg, 1 mmol), methyl acrylate (182 µl 2 mmol), and methanol (2 ml) is stirred for 24 hours at room temperature, concentrated to an oily residue, and chromatographed on silica gel (EtOAc) to give trans-3-[3-methyl-4-[(1-oxopropyl)phenylamino]-piperidine]propanoic acid, methyl ester as an oil: 300 mg; 89%. The monohydrate oxalate salt is made as described in Example 7; oxalate salt monohydrate: m.p. 125°–130° C.

| Elemental Analysis for $C_{21}H_{32}N_2O_8$: | | | |
|---|---|---|---|
| | C % | H % | N % |
| Found: | 57.4 | 7.0 | 6.4 |
| Calculated: | 57.3 | 7.3 | 6.4 |

EXAMPLE 30

Trans-3-[3-methyl-4-[(1-oxopropyl)phenylamino]-piperidine]propanoic acid, ethoxymethyl ester A solution of trans-3-methyl-4-(1-oxopropyl)-phenylamino]-piperidine (300 mg, 1.2 mmol), ethoxymethyl acrylate (350 mg, 2.4 mmol), and acetonitrile (10 ml) is stirred at room temperature for 24 hours, concentrated to an oily residue, and chromatographed on silica gel (EtOAc) to give trans-3-[3-methyl-4-[(1- oxopropyl)phenylamino]piperidine]propanoic acid, ethoxymethyl ester as an oil: 300 mg; 65%. The oxalate salt is made as described in Example 7; oxalate salt: m.p. 115°–116° C.

EXAMPLE 31

Trans-3-[3-methyl-4-[(1-oxopropyl)phenylamino]-piperidine]propanoic acid, allyl ester A solution of trans-3-methyl-4-[(1-oxopropyl)-phenylamino]piperidine (300 mg, 1.2 mmol), allyl acrylate (272 mg, 2.4 mmol) is stirred at room temperature for 16 hours and concentrated to an oily residue which is chromatographed on silica gel (EtOAc) to give trans-3-[3-methyl-4-[(1-oxopropyl)phenylamino]piperidine]-propanoic acid, allyl ester as an oil: 300 mg; 69%. The oxalate salt is made as described in Example 7: oxalate salt: m.p. 147°–148° C.

| Elemental Analysis for $C_{23}H_{32}N_2O_7$: | | | |
|---|---|---|---|
| | C % | H % | N % |
| Found: | 61.7 | 7.2 | 6.2 |
| Calculated: | 61.6 | 7.2 | 6.2 |

EXAMPLE 32

Trans-2-[3-methyl-4-[(1-oxopropyl)phenylamino]-piperidine]ethyl acetate

A mixture of trans-3-methyl-4-[(1-oxopropyl)-phenylamino]piperidine (250 mg, 1 mmol), 2-bromoethyl acetate (338 mg, 2.0 mmol), potassium carbonate (300 mg, 2.2 mmol), sodium iodide (50 mg, 0.3 mmol), and acetonitrile is stirred at room temperature for 16 hours. The resultant mixture is diluted with a saturated solution of sodium bicarbonate (25 ml) and extracted with ethyl acetate (2×25 ml). The organic extracts are combined, dried over magnesium sulfate, and concentrated to an oily residue which is chromatographed on silica gel (EtOAc) to give trans-2-[3-methyl-4-[(1-oxopropyl)phenylamino]piperidine]ethyl acetate as an oil: 300 mg; 89%. The oxalate salt is made as described in Example 7; oxalate salt: m.p. 149°–150° C.

| Elemental Analysis for $C_{21}H_{30}N_2O_7$: | | | |
|---|---|---|---|
| | C % | H % | N % |
| Found:. | 59.6 | 7.2 | 6.6 |
| Calculated: | 59.7 | 7.2 | 6.6 |

EXAMPLE 33

(±)-Cis-3-methyl-4-[(1-oxopropyl)-2-fluoro-phenylamino]piperidine

A solution of 1-methoxycarbonyl-3-methyl-4-(2-fluorophenyl-amino)-piperidine (12.95 g, 48.6 mmol), prepared according to the procedure of W. F. M. Van Berer et al., J. Med. Chem. 1974, 17, 1047 and T. R. Burke, Jr. et al., J. Med. Chem. 1986, 29, 1087, except that 2-fluoroaniline was substituted for aniline, and propionic anhydride (12.5 ml, 7.2 mmol) is refluxed for fifteen hours. The cooled solution is diluted with ethyl acetate and washed with 2N sodium hydroxide (2×), saturated sodium bicarbonate (5×), 1M phosphoric acid (1×) and brine (1×). The organics are dried over sodium sulfate and then concentrated. The residue is dissolved in ether and hexanes and cooled to ×10° C. for fifteen hours. The solid that precipitated is collected and recrystallized from ether and hexanes to give cis-1-methoxycarbonyl-3-methyl-4-[(1-oxopropyl)-2-fluorophenylamino]piperidine as a solid: 3.2 g; 20%; m.p. 128°–130° C. The mother liquors are combined and concentrated to give a mixture of cis and trans isomers along with some other impurities.

A suspension of cis-1-methoxycarbonyl-3-methyl-4-[(1-oxo-propyl)-2-fluorophenylamino]-piperidine (3.2 g, 9.89 mmol) in 48% aqueous HBr (20 ml) is refluxed for two hours. Upon heating the mixture dissolution occurs. The solution is cooled to 0° C. and 5N NaOH is added until the pH is between 11 and 12. The aqueous phase is extracted with methylene chloride (5×) and the combined organics dried over sodium sulfate and concentrated to give cis-3-methyl-4-(2-fluoro-phenylamino)-piperidine as an oil: 2.0 g; 97%.

To a rapidly stirred mixture of benzylchloroformate (0.39 ml, 2.76 mmol) and sodium bicarbonate (284 mg, 3.6 mmol) in water (4 ml) and ether (4 ml) is added cis-3-methyl-4-(2-fluoro-phenylamino)-piperidine (500 mg, 2.4 mmol) as a solution in ether (2 ml). The mixture is stirred for one hour at ambient temperature, the layers are separated, and the organics washed with 2N NaOH (2×) and brine (1×). The organics are dried over sodium sulfate and concentrated to give cis-1-benzyloxycarbonyl-3-methyl-4-(2-fluorophenylamino)-piperidine as an oil: 740 mg; 90%.

To a solution of cis-1-benzyloxycarbonyl-3-methyl-4-(2-fluoro-phenylamino)-piperidine (740 mg, 2.16 mmol) and 4-dimethylaminopyridine (395 mg, 3.24 mmol) in acetonitrile (10 ml) is added propionyl chloride (0.38 ml, 4.32 mmol). The reaction is heated to 50° C. for ten hours. The mixture is concentrated and the residue dissolved in ethyl acetate and water. The organic phase is washed with saturated sodium bicarbonate (2×), 1M phosphoric acid (1×), and brine (1×). The organics are dried over sodium sulfate and concentrated to give pure cis-1-benzyloxycarbonyl-3-methyl-4-[(1-oxopropyl)-2-fluorophenylamino-piperidine as an oil: 769 mg; 89%.

A mixture of cis-1-benzyloxycarbonyl-3-methyl-4-[(1-oxopropyl)-2-fluorophenylamino]-piperidine (576 mg, 1.45 mmol) and 10% Pd-C (100 mg) in methanol (25 ml) and acetic acid (5 ml) is hydrogenated at 50 psi for five hours. The reaction mixture is filtered through celite and the filtrate is concentrated. The residue is diluted with ethyl acetate, basified to pH 11 with 2N NaOH and shaken. The separated organics are dried over sodium sulfate and concentrated to give cis-3-methyl-4-[(1-oxopropyl)-2-fluorophenylamino]piperidine as an oil: 333 mg; 87%.

EXAMPLE 34

(±)-Cis-3-[3-methyl-4-(1-oxopropyl)-2-fluoro-phenylamino]-1-piperidine]propionic acid, methyl ester A solution of (±)-cis-3-methyl-4-[(1-oxopropyl)-2fluorophenylamino]-piperidine (200 mg, 0.757 mmol) and methyl acrylate (0.1 ml, 1.13 mmol) in acetonitrile (2 ml) is stirred at room temperature for twelve hours. The solution is concentrated and the residue chromatographed on silica gel (2/1 EtOAc/Hex) to yield (±)-cis-3-[3-methyl-4-[(1-oxopropyl)-2-fluorophenylamino]-1-piperidine]propanoic acid, methyl ester as an oil: 44 mg, 17% yield. The hydrochloride salt is prepared by bubbling gaseous HCl through a toluene solution of the free base and concentrating to a white solid; hydrochloride salt: m.p. 177°–178° C.;

| Elemental Analysis for $C_{19}H_{28}N_2O_3ClF$: | | | |
|---|---|---|---|
| | C % | H % | N % |
| Found: | 59.0 | 7.3 | 7.2 |
| Calculated: | 59.0 | 7.3 | 7.2 |

EXAMPLE 35

(±)-Cis-3-[3-methyl-4-[(1-oxopropyl)-2-fluorophenylamino]-1-piperidine]propanoic acid, ethoxymethyl ester A solution of (±)-cis-3-methyl-4-[(1-oxopropyl)-2-fluorophenylamino]-piperidine (70 mg, 0.265 mmol) and ethoxymethyl acrylate (73 μl, 0.265 mmol) in acetonitrile (1 ml) is stirred at room temperature for eighteen hours. The solution is concentrated and the residue chromatographed on silica gel (EtOAc) to give (±)-cis-3-[3-methyl-4-[(1-oxopropyl)-2-fluorophenylamino]-1-piperidine]propanoic acid, ethoxymethyl ester as an oil: 84 mg, 80% yield. The oxalate salt is made by dissolving the free base in ethyl acetate and adding an ethereal solution of oxalic acid. The gum that precipitates is redissolved in hot ethyl acetate and recrystallizes to give a white solid upon cooling; oxalate salt: m.p. 96°–97° C.;

| Elemental Analysis for $C_{23}H_{33}N_2O_8F$: | | | |
|---|---|---|---|
| | C % | H % | N % |
| Found: | 56.6 | 6.8 | 6.1 |
| Calculated: | 57.0 | 6.9 | 5.8 |

EXAMPLE 36

(±)-Cis-3-[3-methyl-4-[(1-oxopropyl)-2-fluorophenylamino-1-piperidine]propanoic acid, allyl ester A solution of (±)-cis-3-methyl-4-[(1-oxopropyl)-2-fluorophenylamino]-piperidine (100 mg, 0.378 mmol) and allyl acrylate (90 ml, 0.757 mmol) in acetonitrile (1 ml) is stirred at room temperature for sixteen hours. The solvent is removed and the residue chromatographed on silica gel (1/1 EtOAc/Hex) to give (±)-cis-3-[3-methyl-4-(1-oxopropyl)-2-fluorophenylamino]-1-piperidine]propanoic acid, allyl ester as an oil: 76 mg, 53%. The oxalate salt monohydrate is made by dissolving the free base in ethyl acetate and then adding an ethereal solution of oxalic acid. The white solid that precipitates is collected and washed with ether and ethyl acetate; oxalate salt monohydrate: m.p. 96°–98° C.;

| Elemental Analysis for $C_{23}H_{33}N_2O_8F$: | | | |
|---|---|---|---|
| | C % | H % | N % |
| Found: | 57.3 | 6.7 | 5.8 |
| Calculated: | 57.0 | 6.9 | 5.8 |

EXAMPLE 37

(±)-Cis-2-[3-methyl-4-[(1-oxopropyl)-2-fluorophenylamino]-1-piperidine]ethyl acetate A suspension of (±)-cis-3-methyl-4-[(1-oxopropyl)-2-fluorophenylamino]-piperidine (250 mg, 0.946 mmol), 2-bromoethyl acetate (0.16 ml, 1.42 mmol), potassium carbonate (260 mg, 1.89 mmol) and a catalytic amount of sodium iodide in acetonitrile (3 ml) is stirred at 45° C. for ten hours. The mixture is diluted with water and ethyl acetate. The aqueous is extracted with ethyl acetate (2×) and the combined organics washed with brine (1×), then dried over sodium sulfate and concentrated. The residue is chromatographed on silica gel (EtOAc) to give (±)-cis-2-[3-methyl-4-[(1-oxopropyl)-2-fluorophenylamino]-1-piperidine]ethyl acetate as an oil: 241 mg, 73%. The oxalate salt hemihydrate is made as described in Example 7; oxalate salt hemihydrate: m.p. 118°–127° C.;

| Elemental Analysis for $C_{21}H_{29}N_2O_7F \cdot 0.5H_2O$: | | | |
|---|---|---|---|
| | C % | H % | N % |
| Found: | 55.7 | 6.6 | 6.2 |
| Calculated: | 56.1 | 6.7 | 6.2 |

EXAMPLE 38

A pharmaceutical composition for parenteral or intravenous analgesic administration can be prepared from the following ingredients:

| Ingredients | Amount |
|---|---|
| 3-[4-Methoxycarbonyl-4-[(1-(oxopropyl)-phenylamino]-1-piperidine]-propanoic acid, methyl ester, HCl salt | 1 mg |
| Isotonic saline | 1 liter |

Other compounds on of course can be substituted for the foregoing specific compound, utilizing a relative amount of such other compounds in the composition depending on the effective analgesic activity of the particular compound.

EXAMPLE 39

The compounds of formula (I) listed in Table III are prepared by following the procedures described herein using equivalent amounts of appropriate starting materials.

TABLE III

| | X | R | R¹ | R² | Ar | salt | m.p. (°C.) |
|---|---|---|---|---|---|---|---|
| a. | —(CH₂)₂COOMe | Et | H | H | 2,4-di-F-Ph | oxalate | 177–178 |
| b. | —(CH₂)₂COOnBu | Et | H | H | 2,4-di-F-Ph | oxalate | 181–182 |
| c. | —(CH₂)₂COOtBu | Et | H | H | 2-F-Ph | oxalate | 160–162 |
| d. | —(CH₂)₂COOMe | Et | H | H | 2-MeO-Ph | oxalate | 139–140 |
| e. | —(CH₂)₂COO(CH₂)₂OMe | Et | H | H | Ph | oxalate | 164–165 |
| f. | —(CH₂)₂COO(CH₂)₂OEt | Et | H | H | Ph | oxalate | 140–141 |
| g. | —(CH₂)₂COOCH₂OMe | Et | H | H | 2-F-Ph | oxalate | 131–133 |
| h. | —CH(CH₃)CH₂COOMe | Et | H | H | Ph | oxalate | 148–149.5 |
| i. | —CH₂CH(CH₃)COOMe | Et | H | H | Ph | oxalate | 146–148 |
| j. | —(CH₂)₂COOMe | Me | H | H | 2-Me-Ph | oxalate | — |

TABLE III-continued

| X | R | R¹ | R² | Ar | salt | m.p. (°C.) |
|---|---|---|---|---|---|---|
| k. —(CH₂)₂COOCH₂OMe | Et | H | H | 2-Et-Ph | oxalate | — |
| l. —(CH₂)₂COOMe | Me | MeO—CO— | H | Ph | HCl | — |
| m. —(CH₂)₂COOMe | Me | MeO—CH₂— | H | Ph | HCl | — |
| n. —(CH₂)₂COOMe | Me | H | cis(±)-Me | 4-CF₃-Ph | oxalate | — |
| o. —(CH₂)₂COOMe | Et | H | cis(±)-Me | 2-Cl-Ph | oxalate | — |

EXAMPLES 40–53

Following the procedure of Example 10 and substituting an equivalent amound of the appropriate alkyl acrylate for the methyl acrylate of Example 10, the following compounds of formula (I) are obtained with melting points for the oxalate salt being indicated below:

40.  3-[4-methoxycarbonyl-4-[(1-oxopropyl)-phenylamino]-1-piperidine]propanoic acid, ethyl ester m.p. 166°–167° C.

41.  3-[4-methoxycarbonyl-4-[(1-oxopropyl)-phenylamino]-1-piperidine]propanoic acid, propyl ester m.p. 169°–170° C.

42.  3-[4-methoxycarbonyl-4-[(1-oxopropyl)-phenylamino]-1-piperidine]propanoic acid, isopropyl ester m.p. 176°–177° C.

43.  3-[4-methoxycarbonyl-4-[(1-oxopropyl)-phenylamino]-1-piperidine]propanoic acid, n-butyl ester m.p. 153°–154° C.

44.  3-[4-methoxycarbonyl-4-[(1-oxopropyl)-phenylamino]-1-piperidine]propanoic acid, iso-butyl ester m.p. 177°–178° C.

45.  3-[4-methoxycarbonyl-4-[(1-oxopropyl)-phenylamino]-1-piperidine]propanoic acid, sec-butyl ester m.p. 160°–161° C.

46.  3-[4-methoxycarbonyl-4-[(1-oxopropyl)-phenylamino]-1-piperidine]propanoic acid, n-pentyl ester m.p. 141°–142° C.

47.  3-[4-methoxycarbonyl-4-[(1-oxopropyl)-phenylamino]-1-piperidine]propanoic acid, 2-methylbutyl ester m.p. 162°–163° C.

48.  3-[4-methoxycarbonyl-4-[(1-oxopropyl)-phenylamino]-1-piperidine]propanoic acid, isopentyl ester m.p. 148°–149° C.

49.  3-[4-methoxycarbonyl-4-[(1-oxopropyl)-phenylamino]-1-piperidine]propanoic acid, neopentyl ester m.p. 157°–158° C.

50.  3-[4-methoxycarbonyl-4-[(1-oxopropyl)-phenylamino]-1-piperidine]propanoic acid, hexyl ester m.p. 141°–142° C.

51.  3-[4-methoxycarbonyl-4-[(1-oxopropyl)-phenylamino]-1-piperidine]propanoic acid, heptyl ester m.p. 129°–130° C.

52.  3-[4-methoxycarbonyl-4-[(1-oxopropyl)-phenylamino]-1-piperidine]propanoic acid, octyl ester m.p. 141°–142° C.

53.  3-[4-methoxycarbonyl-4-[(1-oxopropyl)-phenylamino]-1-piperidine]propanoic acid, tert-butyl ester m.p. 157°–158° C.

In the synthesis procedure of Examples 40–53, the alkyl acrylate starting material may be available commercially, may be synthesized by literature procedures or may be synthesized by the following procedure, substituting an equivalent amount of the appropriate alcohol for 3-methyl butanol:

To a stirred solution of 3-methyl butanol (2.0 g, 22.6 mmol) and acryloyl chloride (2.05 g, 22.6 mmol) in dichloromethane (5 ml) at 0° C. is added dropwise triethylamine (3.2 ml, 22.7 mmol). The solution is stirred for 30 minutes at room temperature and then concentrated to a residue. The residue is washed with hexanes (2×10 ml) and the resultant combined organics are concentrated and filtered through a plug of silica to give 3.0 g of 3-methylbutyl acrylate as an oil, 93% yield.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A compound having the formula (I):

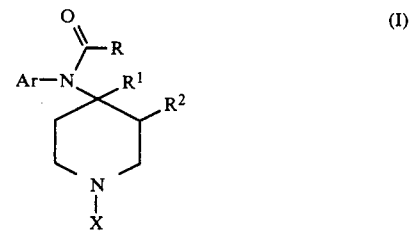

wherein
X is a member selected from the group consisting of: alkoxy-carbonyl-lower alkyl, lower alkyl-carbonyloxy-lower alkyl, alkenyloxy-carbonyl-lower alkyl, and $(C_{1-2})$alkoxy-$(C_{1-2})$alkoxy-carbonyl-lower alkyl Ar is a member selected from the group consisting of phenyl and mono- di- and tri-substituted phenyl, wherein each substituent is independently selected from the group consisting of halo, lower alkyl, lower alkoxy and trifluoromethyl;

R is a member selected from the group consisting of lower alkyl, and lower alkoxy-lower alkyl;

R¹ is a member selected from the group consisting of hydrogen, lower alkoxy-carbonyl, and methoxymethyl; and R² is a member selected from the group consisting of hydrogen and methyl;

and the diastereomeric and enantiomeric isomers thereof, and the pharmaceutically acceptable acid addition salts of said compounds and isomers.

2. The compound of claim 1 wherein X is alkoxy-carbonyl-lower alkyl.

3. The compound of claim 1 wherein X is lower alkyl-carbonyl-oxy-lower alkyl.

4. The compound of claim 1 wherein X is alkenyloxy-carbonyl-lower alkyl.

5. The compound of claim 1 wherein X is $(C_{1-2})$alkoxy-$(C_{1-2})$-alkoxy-carbonyl-lower alkyl.

6. The compound of claim 1 wherein Ar is phenyl or 2-fluorophenyl.

7. The compound of claim 1 wherein R is ethyl.

8. The compound of claim 1 wherein R¹ is methoxycarbonyl.

9. The compound of claim 1, wherein said compound is:

5-[4-methoxycarbonyl-4-[(1-oxopropyl)phenylamino]-1-piperidine]pentanoic acid, methyl ester;
2-[4-methoxycarbonyl-4-[(1-oxopropyl)phenylamino]-1-piperidine]ethyl acetate;
3-[4-[(1-oxopropyl)-2-fluorophenylamino]-1-piperidine]propanoic acid, methyl ester; or
3-[4-methoxycarbonyl-4-[(1-oxopropyl)phenylamino]-1-piperidine]propanoic acid, vinyl ester, or pharmaceutically acceptable acid addition salt thereof.

10. 3-[4-Methoxycarbonyl-4-[(1-oxopropyl)-phenylamino]-1-piperidine]propanoic acid, alkyl ester, and the pharmaceutically acceptable acid addition salts thereof.

11. The compound of claim 10, wherein in the alkyl portion of the said alkyl ester, the carbon directly attached to the oxygen is a methylene or methyl group.

12. The compound of claim 10, wherein said alkyl of said alkyl ester is of about 1 to 10 carbons.

13. The compound of claim 10, wherein said alkyl ester is the methyl ester.

14. A diastereomer or enantiomer of a compound as claimed in claim 1.

15. A pharmaceutical analgesic composition comprising an effective analgesic amount of a compound having the formula (I):

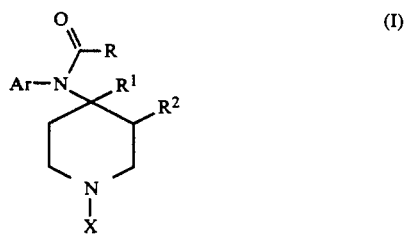

wherein:
X is a member selected from the group consisting of: alkoxy-carbonyl-lower alkyl, lower alkyl-carbonyloxy-lower alkyl, alkenyloxy-carbonyl-lower alkyl, and $(C_{1-2})$alkoxy-$(C_{1-2})$alkoxy-carbonyl-lower alkyl;
Ar is a member selected from the group consisting of phenyl and mono-, di- and tri-substituted phenyl, wherein each substituent is independently selected from the group consisting of halo, lower alkyl, lower alkoxy and trifluoromethyl;
R is a member selected from the group consisting of lower alkyl, and lower alkoxy-lower alkyl;
$R^1$ is a member selected from the group consisting of hydrogen, lower alkoxy-carbonyl, and methoxymethyl; and
$R^2$ is a member selected from the group consisting of hydrogen and methyl;
and the diastereomeric and enantiomeric isomers thereof, and the pharmaceutically acceptable acid addition salts of said compounds and isomers;
and a pharmaceutically acceptable carrier.

16. The composition of claim 15 wherein X is alkoxycarbonyl-lower alkyl.

17. The composition of claim 15 wherein X is lower alkyl-carbonyloxy-lower alkyl.

18. The composition of claim 15 wherein X is alkenyloxy-carbonyl-lower alkyl.

19. The composition of claim 15 wherein X is $(C_{1-2})$alkoxy-$(C_{1-2})$-alkoxy-carbonyl-lower alkyl.

20. The composition of claim 15 wherein Ar is phenyl or 2-fluorophenyl.

21. The composition of claim 15 wherein R is ethyl.

22. The composition of claim 15 wherein $R^1$ is methoxycarbonyl.

23. The composition of claim 15 wherein said compound is:

5-[4-methoxycarbonyl-4-[(1-oxopropyl)phenylamino]-1-piperidine]pentanoic acid, methyl ester;
2-[4-methoxycarbonyl-4-[(1-oxopropyl)phenylamino]-1-piperidine]ethyl acetate;
3-[4-(1-oxopropyl)-2-fluorophenylamino]-1-piperidine]propanoic acid, methyl ester;
3-[4-methoxycarbonyl-4-[(1-oxopropyl)phenylamino]-1-piperidine]propanoic acid, vinyl ester;

or the pharmaceutically acceptable acid addition salt thereof.

24. 3-[4-Methoxycarbonyl-4-[(1-oxopropyl)-phenylamino]-1-piperidine]propanoic acid, alkyl ester, and the pharmaceutically acceptable acid addition salt thereof.

25. The composition of claim 24 wherein in the alkyl portion of the said alkyl ester, the carbon directly attached to the oxygen is a methylene or methyl group.

26. The composition of claim 24, wherein said alkyl of said alkyl ester is of about 1 to 10 carbons.

27. The composition of claim 24, wherein said alkyl ester is the methyl ester.

28. The composition of claim 15, wherein said compound is a diastereomer or enantiomer.

29. The composition of claim 15, wherein said pharmaceutically acceptable carrier is suitable for parenteral administration.

30. A method of providing analgesia in a mammal comprising administering to such mammal an analgesically effective amount of a compound having the formula (I):

wherein:
X is a member selected from the group consisting of: alkoxy-carbonyl-lower alkyl, lower alkyl-carbonyloxy-lower alkyl, alkenyloxy-carbonyl-lower alkyl, and $(C_{1-2})$alkoxy-$(C_{1-2})$alkoxy-carbonyl-lower alkyl;
Ar is a member selected from the group consisting of phenyl and mono-, di- and tri-substituted phenyl, wherein each substituent is independently selected from the group consisting of halo, lower alkyl, lower alkoxy and trifluoromethyl;
R is a member selected from the group consisting of lower alkyl, and lower alkoxy-lower alkyl;
$R^1$ is a member selected from the group consisting of hydrogen, lower alkoxy-carbonyl, and methoxymethyl; and
$R^2$ is a member selected from the group consisting of hydrogen and methyl;

and the optically active and cis-trans isomers thereof, and the pharmaceutically acceptable acid addition salts of said compounds and isomers.

31. The method of claim 30 wherein X is alkoxy-carbonyl-lower alkyl.

32. The method of claim 30 wherein X is lower alkyl-carbonyloxy-lower alkyl.

33. The method of claim 30 wherein X is alkenyloxy-carbonyl-lower alkyl.

34. The method of claim 30 wherein X is $(C_{1-2})$alkoxy-$(C_{1-2})$-alkoxy-carbonyl-lower alkyl.

35. The method of claim 30 wherein Ar is phenyl or 2-fluorophenyl.

36. The method of claim 30 wherein R is ethyl.

37. The method of claim 30 wherein $R^1$ is methoxycarbonyl.

38. The method of claim 30 wherein said compound is 5-[4-methoxycarbonyl-4-[(1-oxopropyl)phenylamino]-1-piperidine]pentanoic acid, methyl ester;
2-[4-methoxycarbonyl-4-(1-oxopropyl)phenylamino]-1-piperidine]ethyl acetate;
3-[4-[(1-oxopropyl)-2-fluorophenylamino]-1-piperidine]propanoic acid, methyl ester; or
3-[4-methoxycarbonyl-4-[(1-oxopropyl)phenylamino]-1-piperidine]propanoic acid, vinyl ester;
or a pharmaceutically acceptable acid addition salt thereof.

39. 3-[4-Methoxycarbonyl-4-[(1-oxopropyl)-phenylamino]-1-piperidine]propanoic acid, methyl ester, and the pharmaceutically acceptable acid addition salts 40. The method of claim 30, wherein in the alkyl portion of the said alkyl ester, the carbon directly attached to the oxygen is a methylene or methyl group.

41. The method of claim 30, wherein said alkyl of said alkyl ester is of about 1 to 10 carbons.

42. The method of claim 30, wherein said alkyl ester is the methyl ester.

43. The method of claim 30, wherein said compound is a diastereomer or enantiomer.

44. A compound having the formula (A):

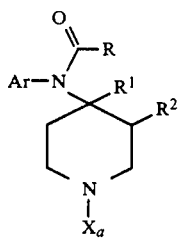

wherein:
$X_a$ is carboxyloweralkyl;
Ar is a member selected from the group consisting of phenyl and mono-, di- and tri-substituted phenyl, wherein each substituent is independently selected from the group consisting of halo, lower alkyl, lower alkoxy and trifluoromethyl;
R is a member selected from the group consisting of lower alkyl, and lower alkoxy-lower alkyl;
$R^1$ is a member selected from the group consisting of hydrogen, lower alkoxy-carbonyl, and methoxymethyl; and
$R^2$ is a member selected from the group consisting of hydrogen and methyl.

45. A compound of claim 44 wherein $X_a$ is carboxyethyl.

46. A compound having the formula (I):

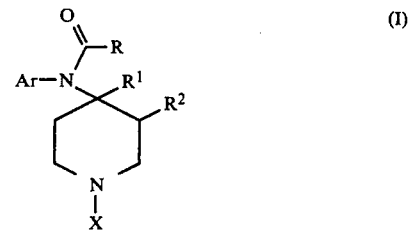

wherein:
X is a member selected from the group consisting of: alkoxy-carbonyl-lower alkyl, lower alkyl-carbonyloxy-lower alkyl, alkenyloxy-carbonyl-lower alkyl, and $(C_{1-2})$alkoxy-$(C_{1-2})$alkoxy-carbonyl-lower alkyl;
Ar is a member selected from the group consisting of phenyl and mono-, di- and tri-substituted phenyl, wherein each substituent is independently selected from the group consisting of halo, lower alkyl, lower alkoxy and trifluoromethyl;
R is a member selected from the group consisting of lower alkyl, and lower alkoxy-lower alkyl;
$R^1$ is a member selected from the group consisting of hydrogen, lower alkoxy-carbonyl, and methoxymethyl; and
$R^2$ is a member selected from the group consisting hydrogen and methyl;
and the diastereomeric and enantiomeric isomers thereof, and the acid addition salts of said compounds and isomers.

47. A compound having the formula:

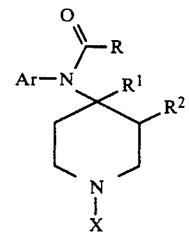

wherein:
X is a member selected from the group consisting of: lower alkoxy-carbonyl-lower alkyl, lower alkyl-carbonyloxy-lower alkyl, lower alkenyloxy-carbonyl-lower alkyl, and $(C_{1-2})$alkoxy -$(C_{1-2})$alkoxy-carbonyl-lower alkyl;
Ar is a member selected from the group consisting of phenyl and mono-, di- and tri-substituted phenyl, wherein each substituent is independently selected from the group consisting of halo, lower alkyl, lower alkoxy and trifluoromethyl;
R is a member selected from the group consisting of lower alkyl, and lower alkoxy-lower alkyl;
$R^1$ is a member selected from the group consisting of hydrogen, lower alkoxy-carbonyl, and methoxymethyl; and
$R^2$ is a member selected from the group consisting of hydrogen and methyl;
and the diastereomeric and enantiomeric isomers thereof, and the pharmaceutically acceptable acid addition salts of said compounds and isomers.

* * * * *

UNITED STATES PATENT AND TRADEMARK OFFICE
CERTIFICATE OF CORRECTION

PATENT NO. : 5,019,583

DATED : May 28, 1991

INVENTOR(S) : Paul L. Feldman, Michael K. James, Marcus F. Brackeen, Michael R. Johnson, Harry J. Leighton It is certified that error appears in the above-identified patent and that said Letters Patent is hereby corrected as shown below:

Column 42:

Claim 24, first line, before "3-[4-Methoxycarbonyl-4-" please insert --The composition of claim 15 wherein said compound is--.

Column 43:

Claim 39, before "3-[4-Methoxycarbonyl-4-" please insert --The method of claim 30 wherein said compound is--.

Signed and Sealed this

Thirteenth Day of August, 1996

Attest:

BRUCE LEHMAN

Attesting Officer

Commissioner of Patents and Trademarks

UNITED STATES PATENT AND TRADEMARK OFFICE

CERTIFICATE EXTENDING PATENT TERM
UNDER 35 U.S.C. § 156

| | | |
|---|---|---|
| PATENT NO. | : | 5,019,583 |
| ISSUED | : | May 28, 1991 |
| INVENTOR(S) | : | Paul L. Feldman et al. |
| PATENT OWNER | : | Glaxo Wellcome Inc. |
| PRODUCT | : | ULTIVA™ (remifentanil hydrochloride) |

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 512 days from February 15, 2009, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 23rd day of October 1998.

Bruce A. Lehman
Assistant Secretary of Commerce and
Commissioner of Patents and Trademarks